(12) United States Patent
Kim et al.

(10) Patent No.: US 11,548,765 B2
(45) Date of Patent: Jan. 10, 2023

(54) LIGHT SOURCE APPARATUS

(71) Applicant: SUZHOU LEKIN SEMICONDUCTOR CO., LTD., Taicang (CN)

(72) Inventors: Dae Hun Kim, Seoul (KR); Sang Hoon Bong, Seoul (KR); Sang Hun An, Seoul (KR); Mi Sun Lee, Seoul (KR)

(73) Assignee: SUZHOU LEKIN SEMICONDUCTOR CO., LTD., Taicang (CN)

( * ) Notice: Subject to any disclaimer, the term of this patent is extended or adjusted under 35 U.S.C. 154(b) by 270 days.

(21) Appl. No.: 16/770,468

(22) PCT Filed: Dec. 7, 2018

(86) PCT No.: PCT/KR2018/015461
§ 371 (c)(1),
(2) Date: Jun. 5, 2020

(87) PCT Pub. No.: WO2019/112356
PCT Pub. Date: Jun. 13, 2019

(65) Prior Publication Data
US 2021/0163266 A1    Jun. 3, 2021

(30) Foreign Application Priority Data

Dec. 7, 2017 (KR) .................. 10-2017-0167538
Dec. 28, 2017 (KR) .................. 10-2017-0181923
Dec. 28, 2017 (KR) .................. 10-2017-0181924

(51) Int. Cl.
*A61L 2/10* (2006.01)
*B66B 31/02* (2006.01)
(Continued)

(52) U.S. Cl.
CPC ............. *B66B 29/04* (2013.01); *A61L 2/10* (2013.01); *B66B 31/02* (2013.01); *F21V 29/745* (2015.01);
(Continued)

(58) Field of Classification Search
CPC ................................. B66B 31/02; A61L 2/10
See application file for complete search history.

(56) References Cited

U.S. PATENT DOCUMENTS

2011/0158862 A1    6/2011   Kim et al.
2018/0099842 A1*   4/2018   Kim .................. A61L 2/26

FOREIGN PATENT DOCUMENTS

KR   10-2010-0023254 A     3/2010
KR   10-2013-0124026 A    11/2013
(Continued)

*Primary Examiner* — Sean P Gramling
(74) *Attorney, Agent, or Firm* — Birch, Stewart, Kolasch & Birch, LLP

(57) ABSTRACT

Disclosed in an embodiment is a light source comprising: a housing; a coupling unit which fixes the housing on the target structure; a light source module for emitting light onto the target structure; and a power source module which supplies power to the light source module. The light source module comprises: a first circuit board; a second circuit board disposed on one side of the first circuit board; a third circuit board disposed on another side of the first circuit board; at least one first ultraviolet light emitting element disposed on one surface of the first circuit board; at least one second ultraviolet light emitting element disposed on one surface of the second circuit board; and at least one third ultraviolet light emitting element disposed on one surface of the third circuit board, wherein one surface of the second circuit board and one surface of the third circuit are disposed so as to face each other.

20 Claims, 20 Drawing Sheets

(51) Int. Cl.
  *B66B 29/04*   (2006.01)
  *F21V 29/74*   (2015.01)
  *F21V 33/00*   (2006.01)
(52) U.S. Cl.
  CPC ......... *F21V 33/006* (2013.01); *A61L 2202/11* (2013.01)

(56) References Cited

FOREIGN PATENT DOCUMENTS

| | | | |
|---|---|---|---|
| KR | 10-2014-0145214 A | | 12/2014 |
| KR | 2014145214 A | * | 12/2014 |
| KR | 10-1582229 B1 | | 1/2016 |
| KR | 10-2016-0018915 A | | 2/2016 |
| KR | 10-1665676 B1 | | 10/2016 |
| KR | 10-1696886 B1 | | 2/2017 |

* cited by examiner

【FIG. 1】
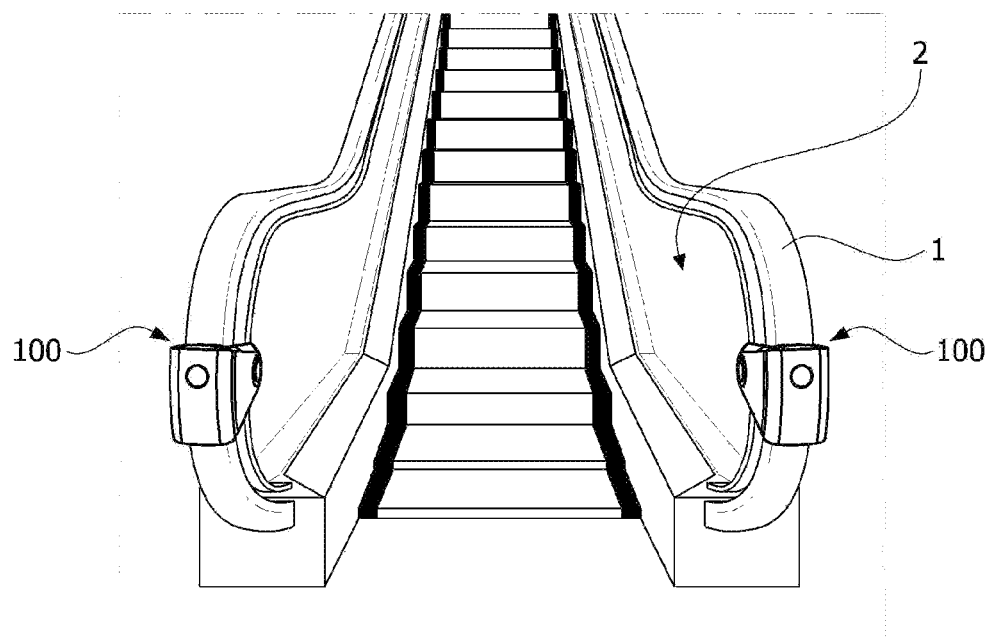

[FIG. 2]
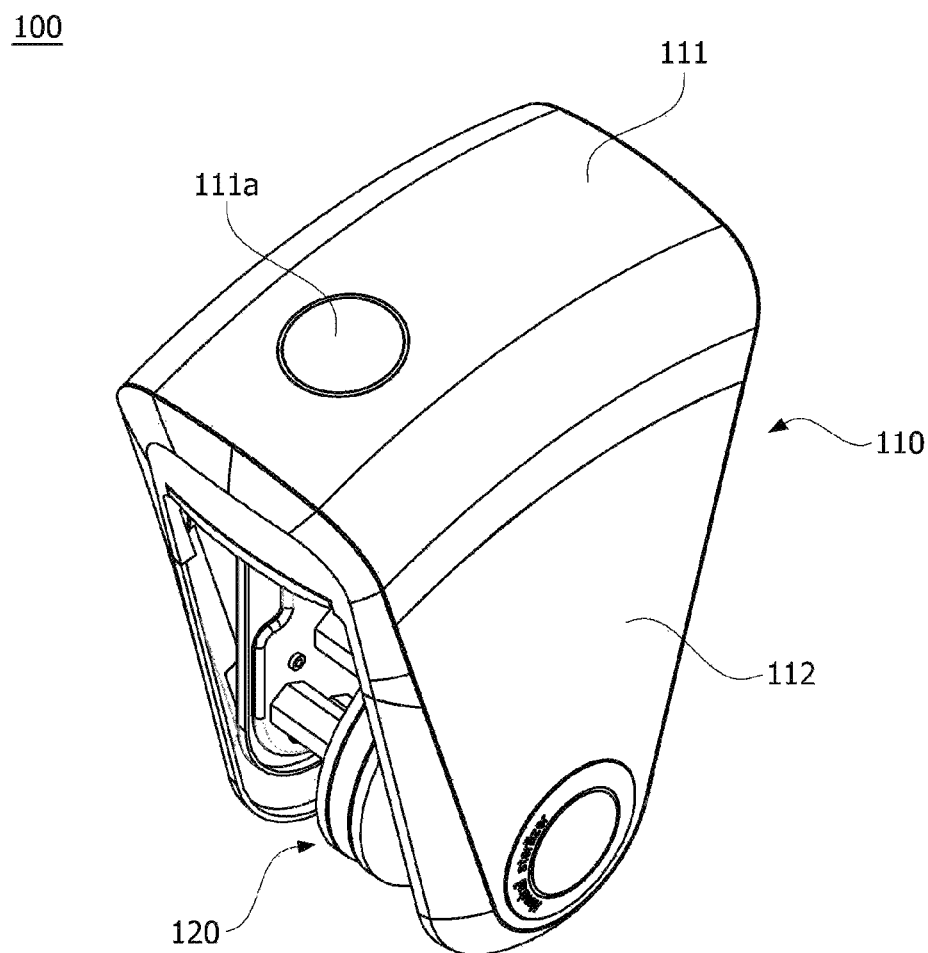

[FIG. 3]
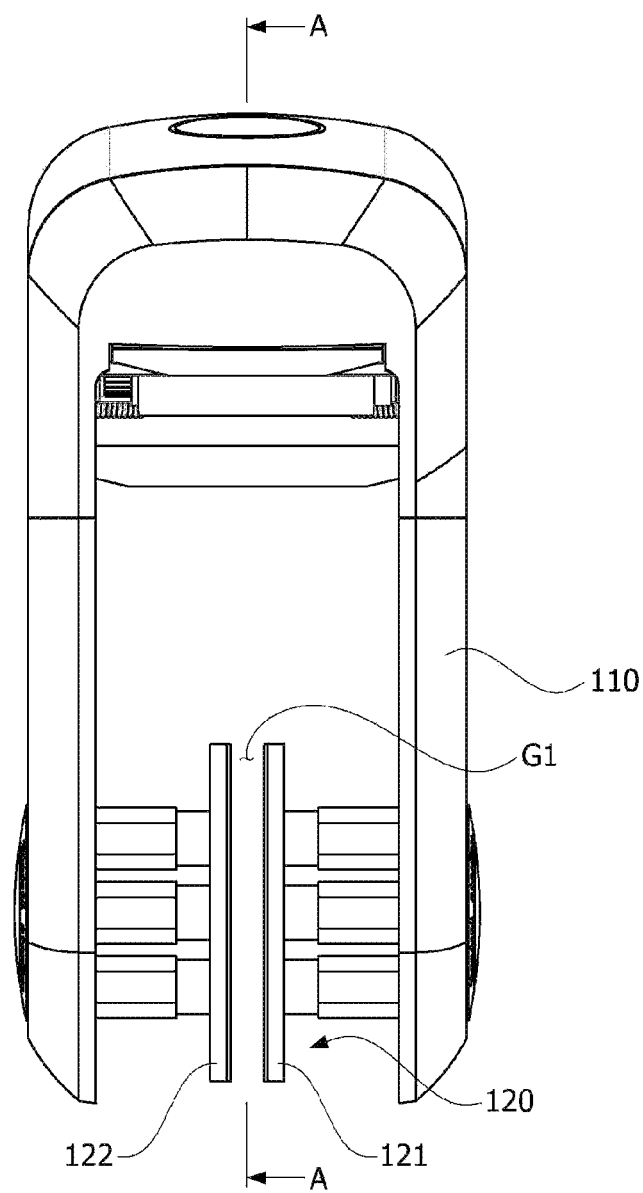

[FIG. 4]
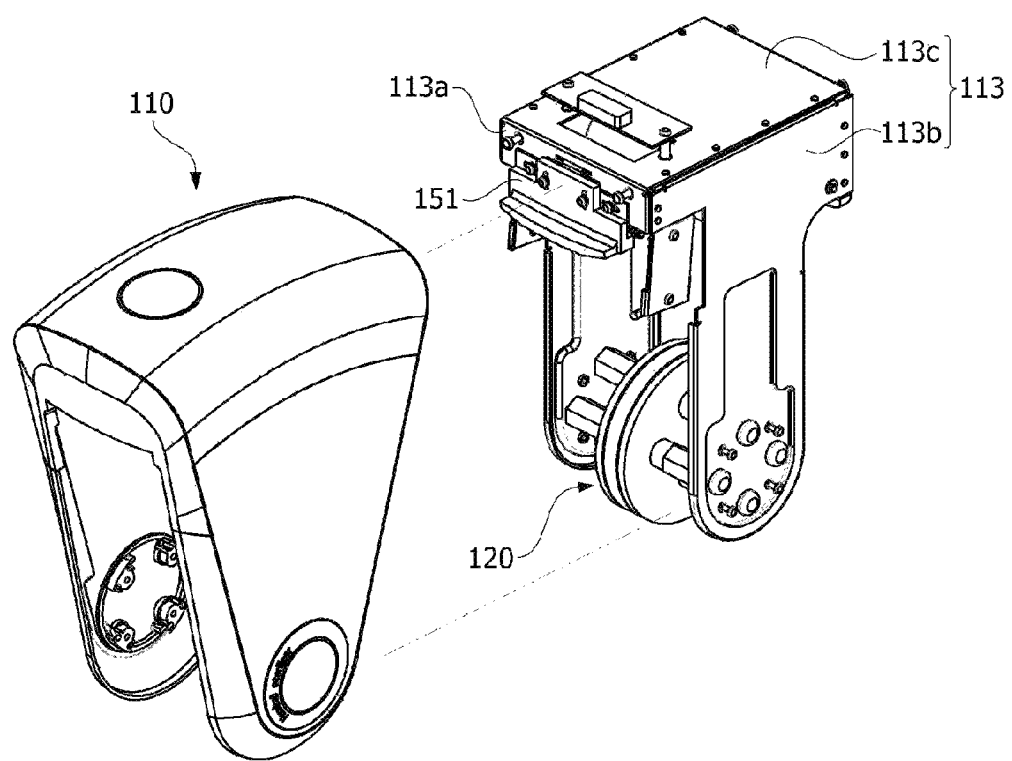

[FIG. 5]
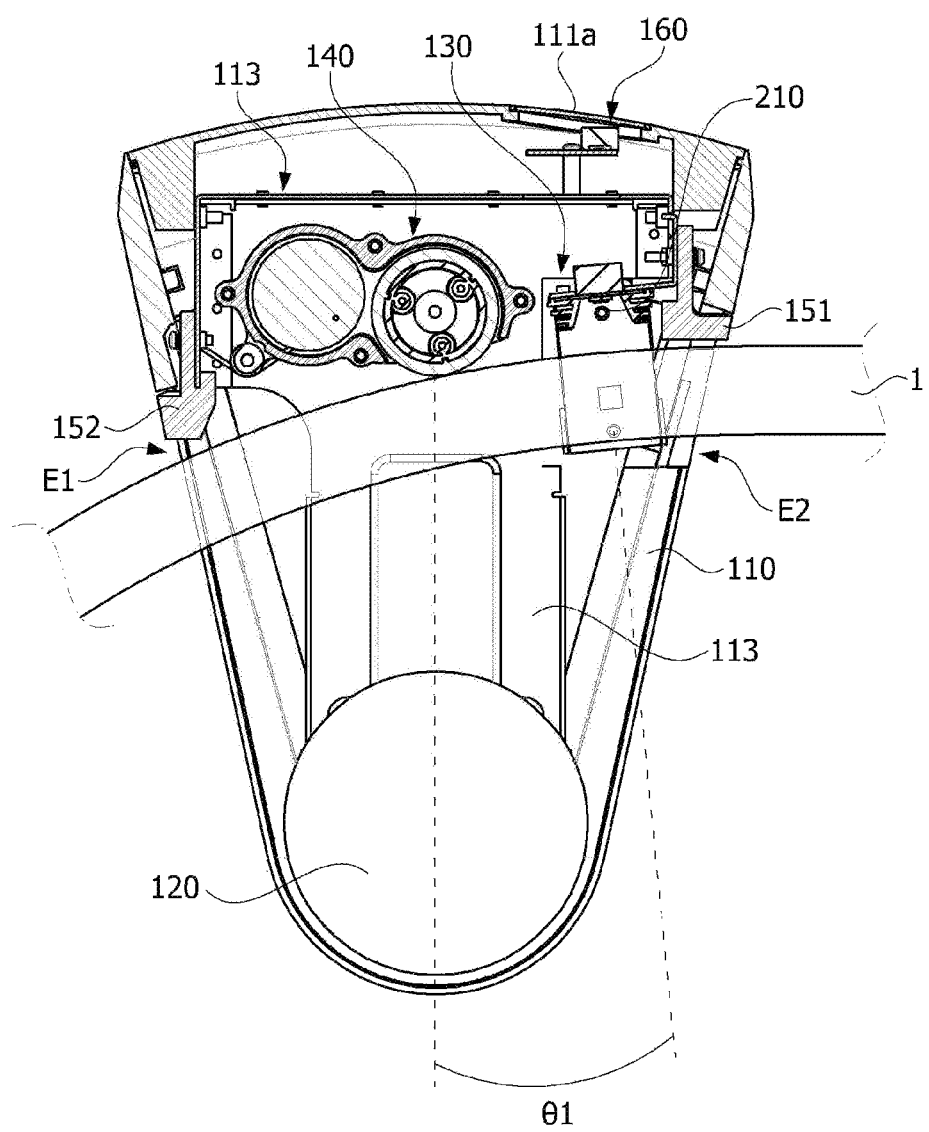

[FIG. 6]
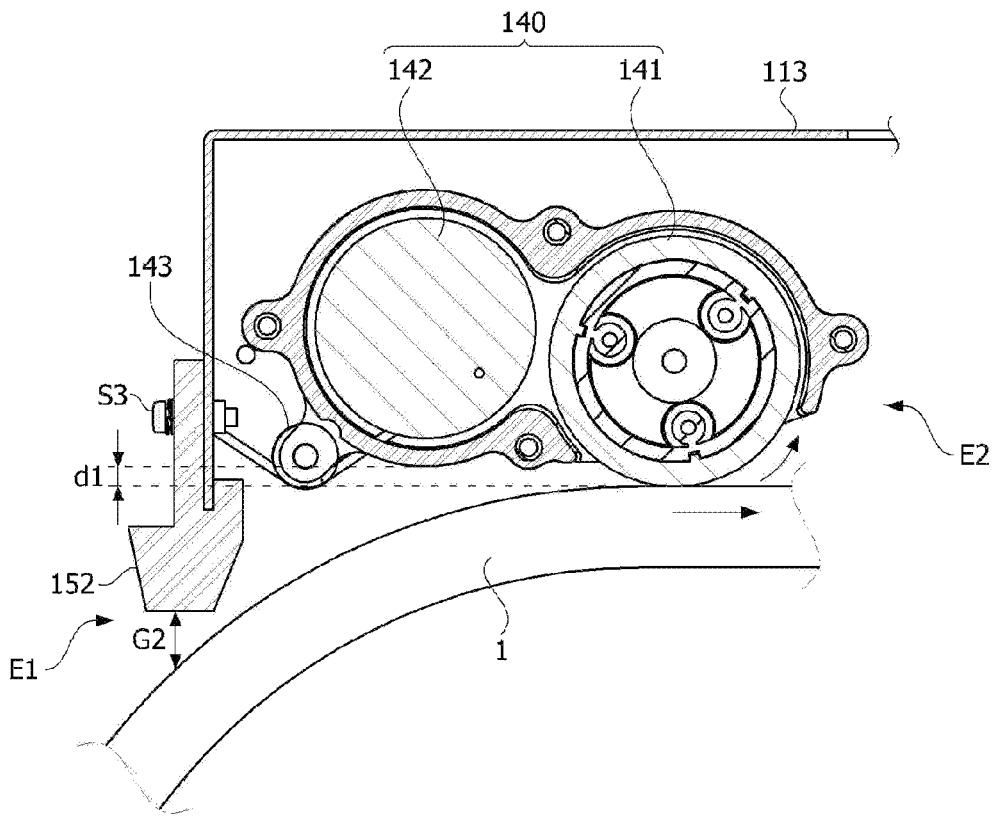
[FIG. 7a]
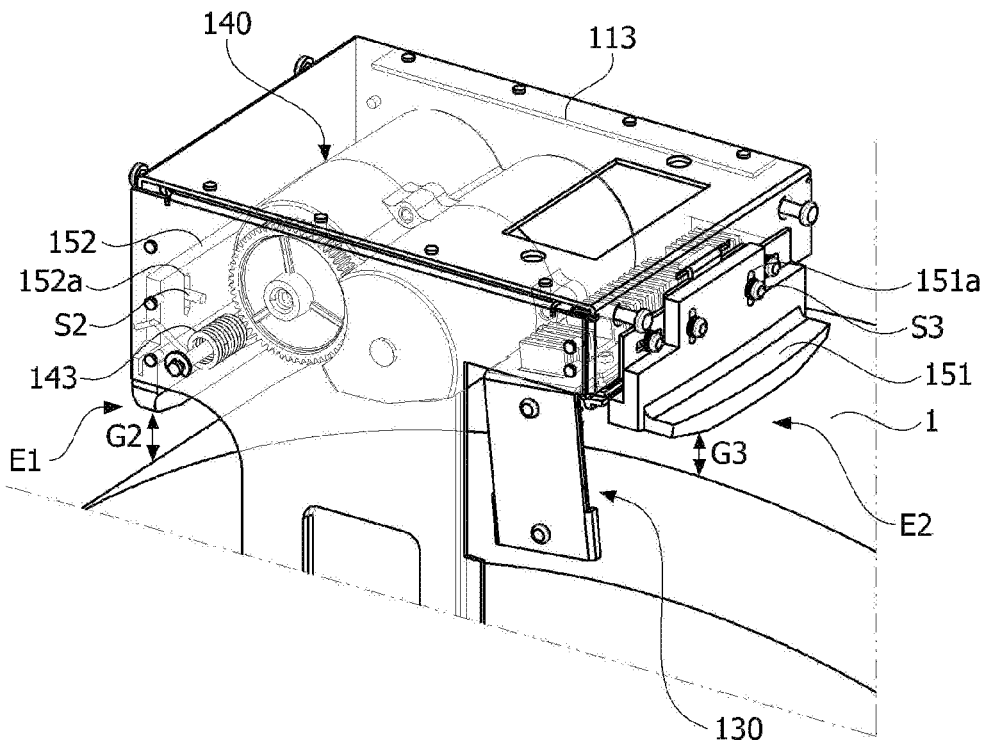

【FIG. 7b】
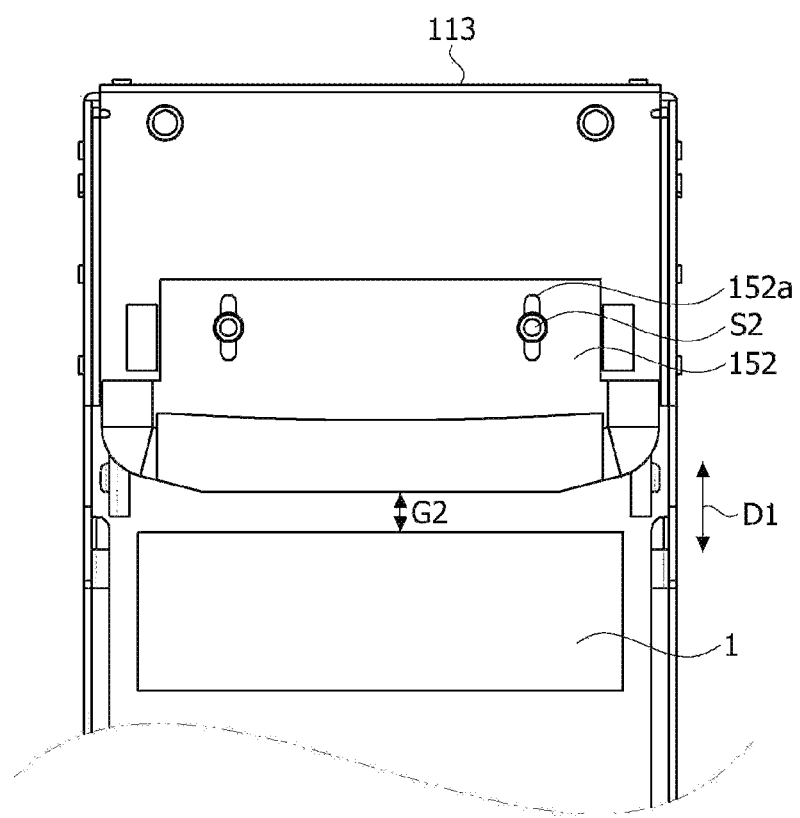

[FIG. 7c]
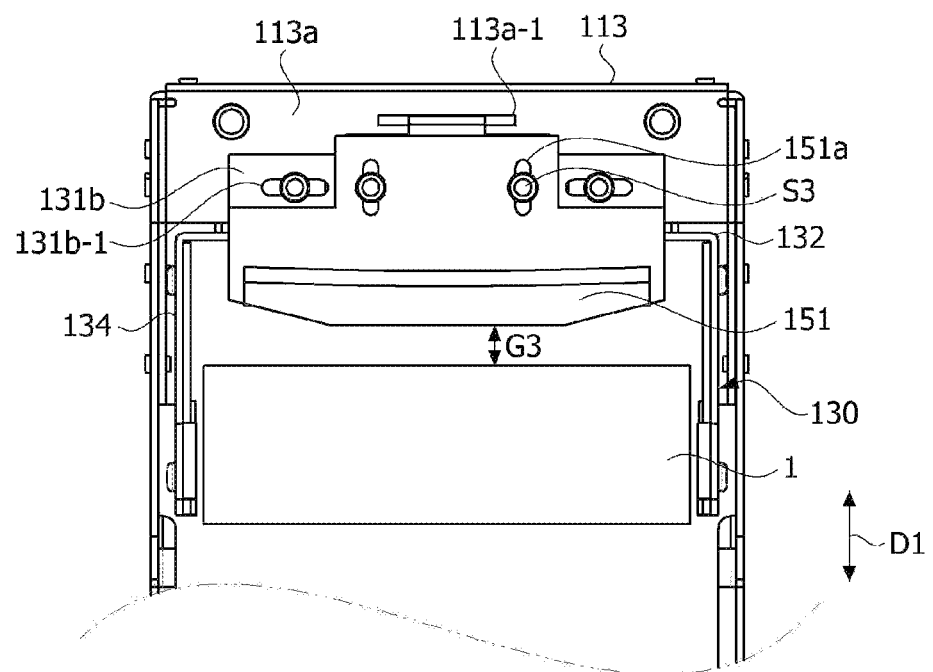

[FIG. 8]
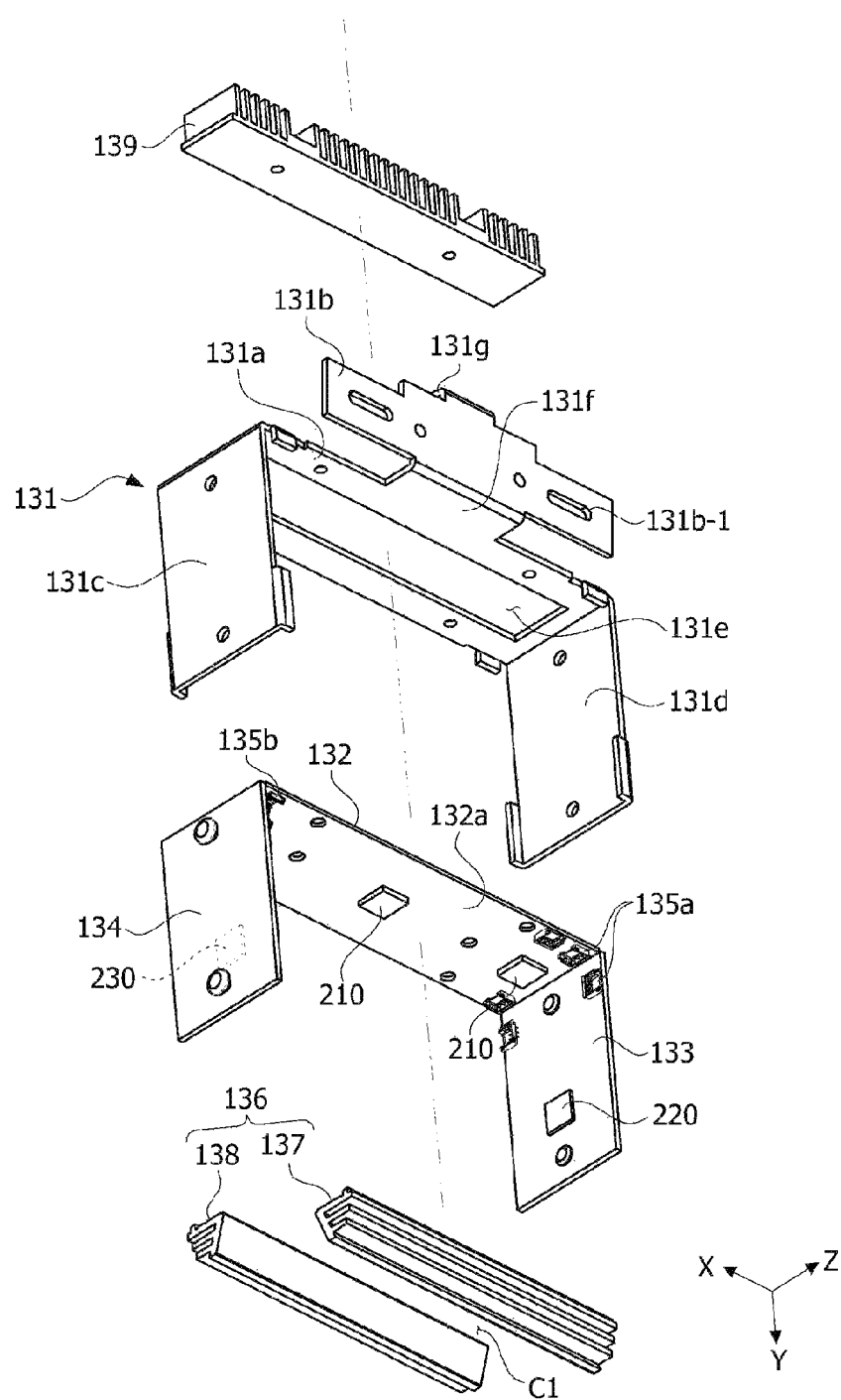

[FIG. 9]
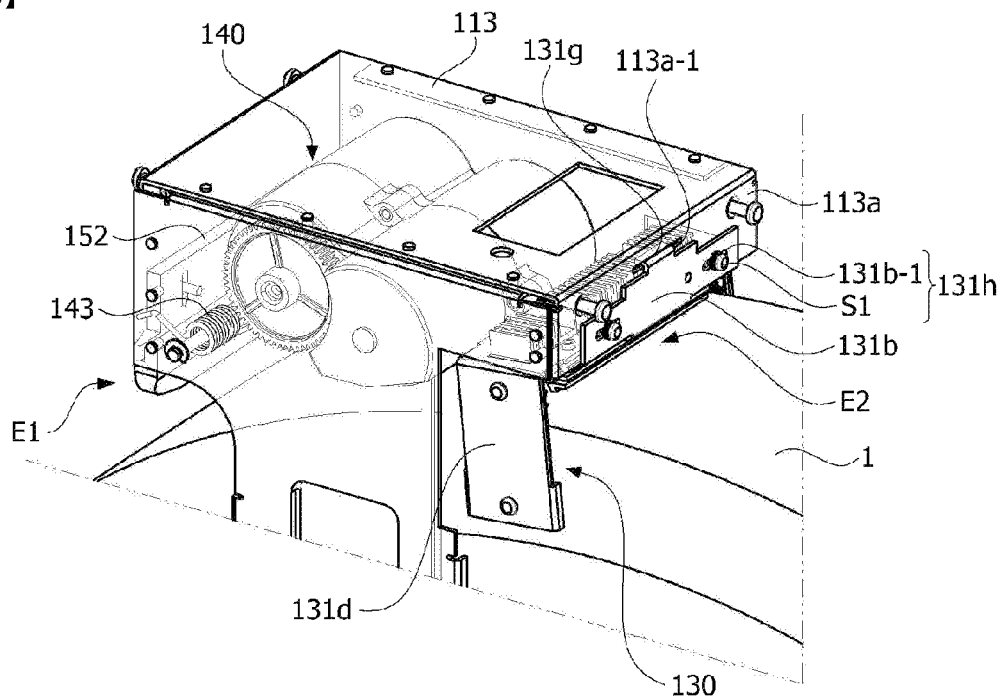
[FIG. 10]
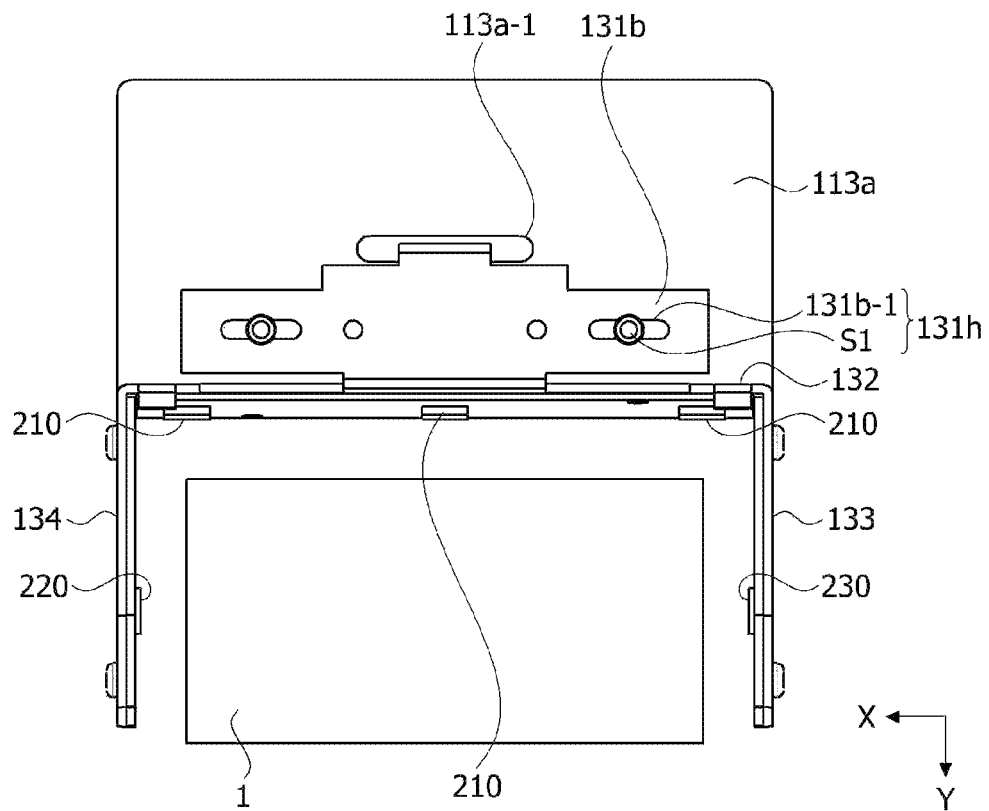

[FIG. 11]
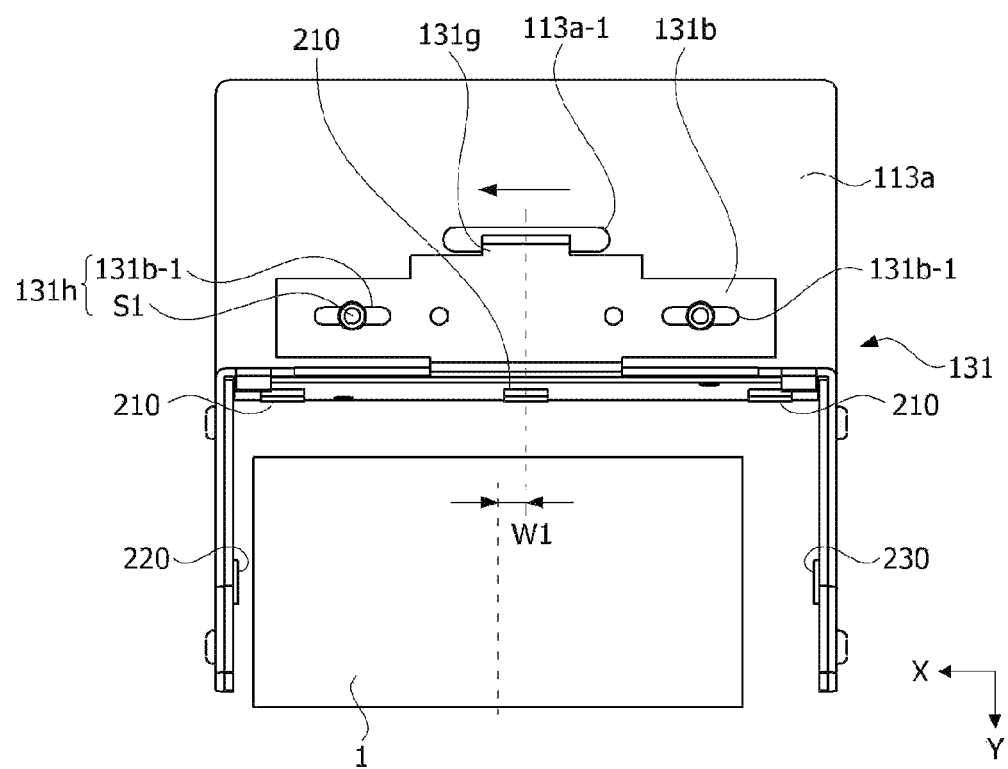

[FIG. 12]
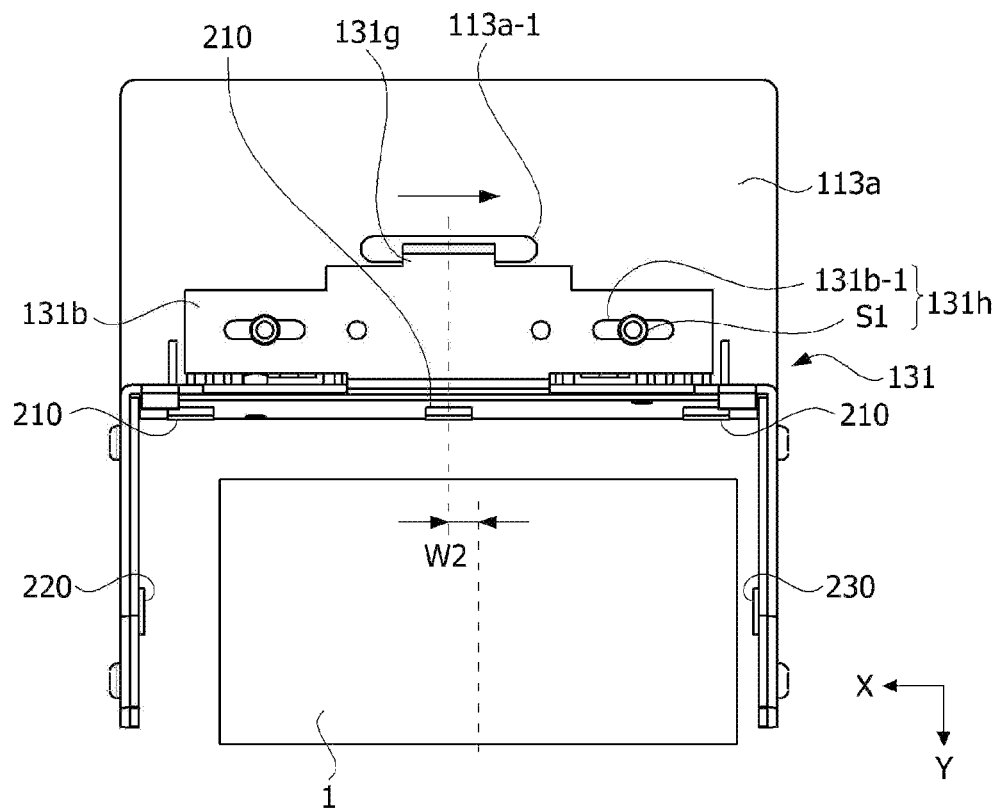
[FIG. 13]
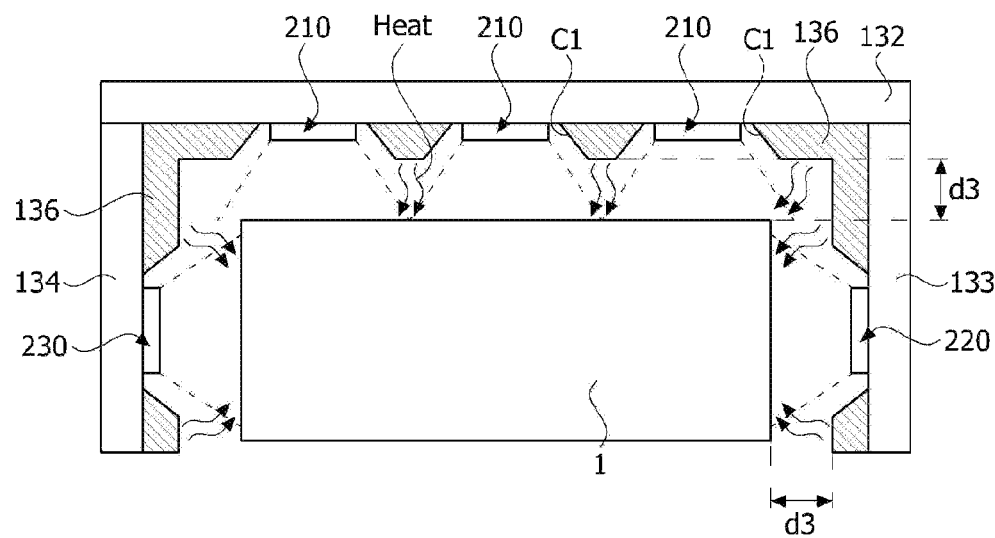

[FIG. 14]
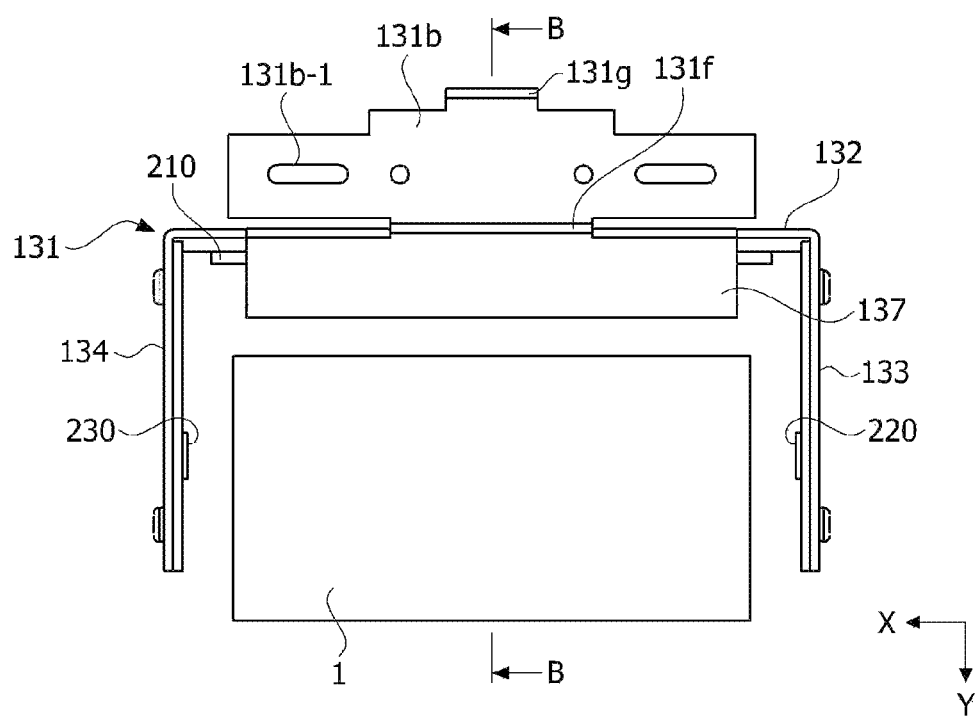

[FIG. 15]
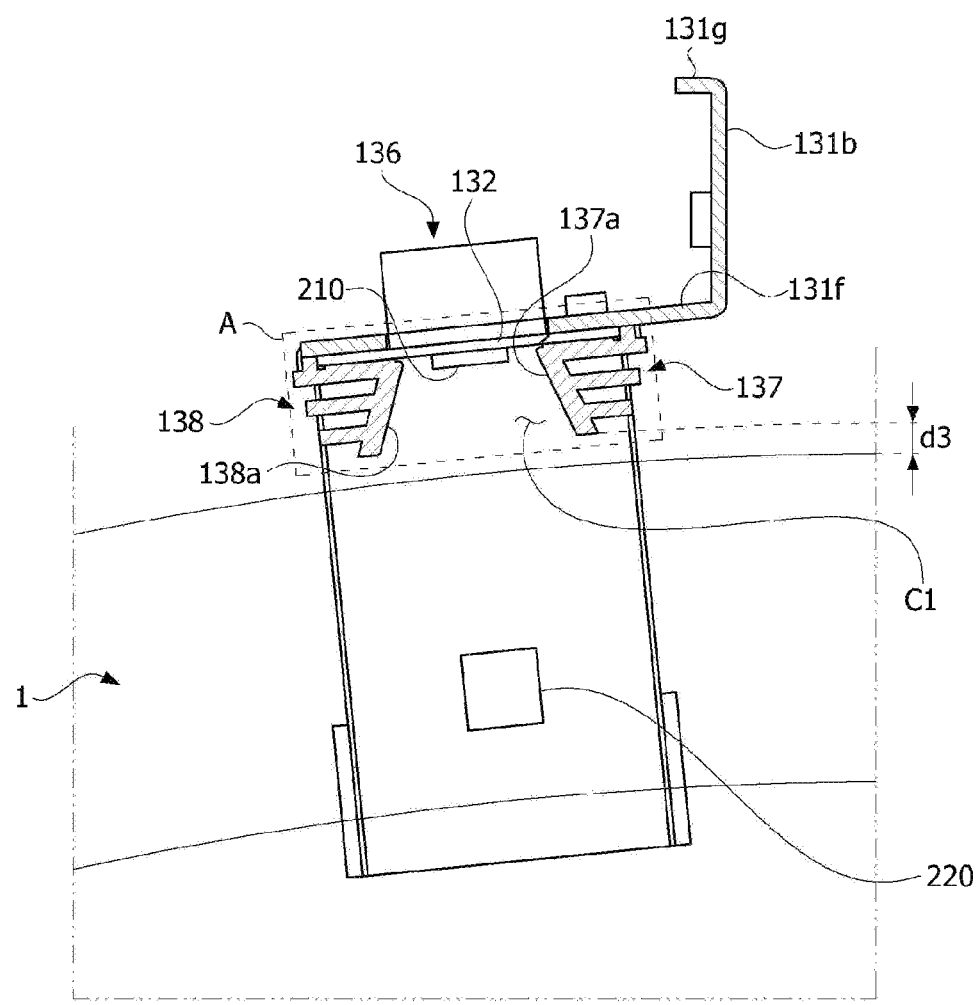

[FIG. 16]
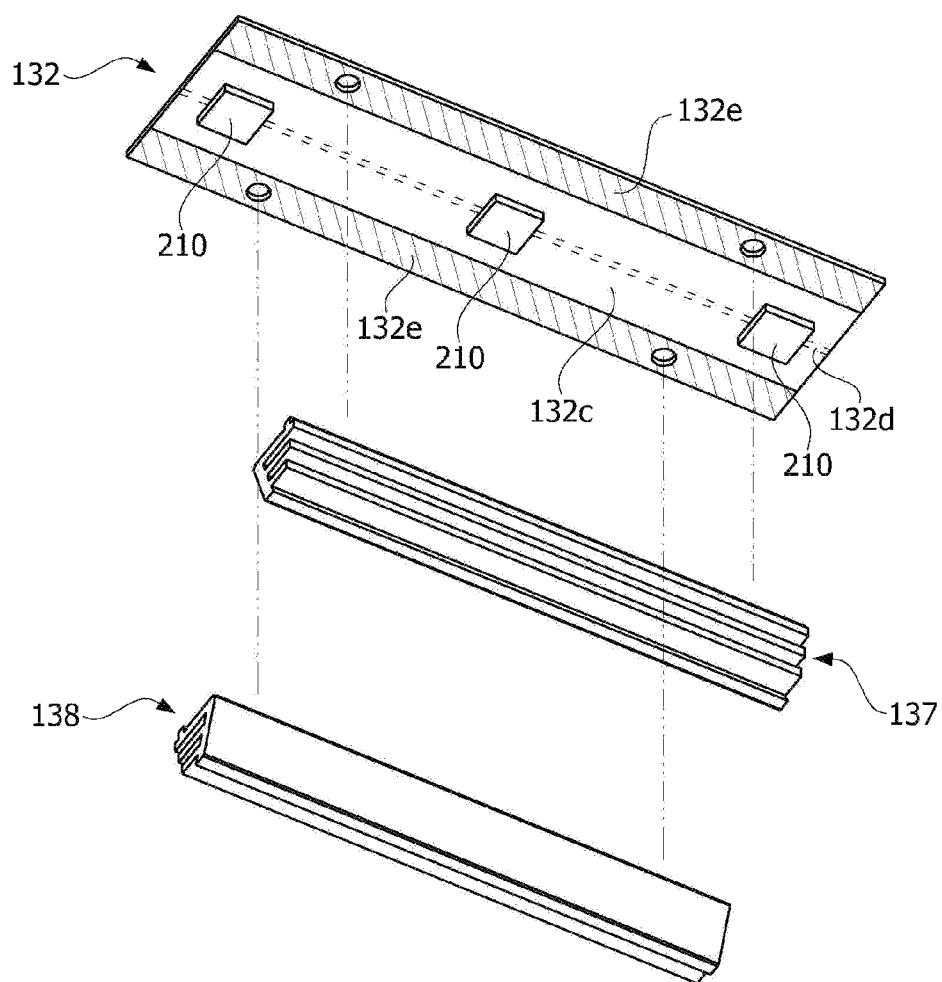

【FIG. 17】
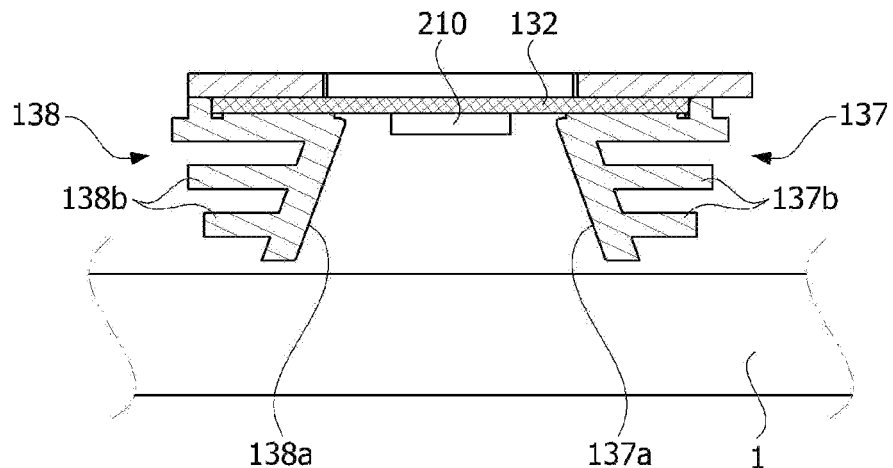
【FIG. 18】
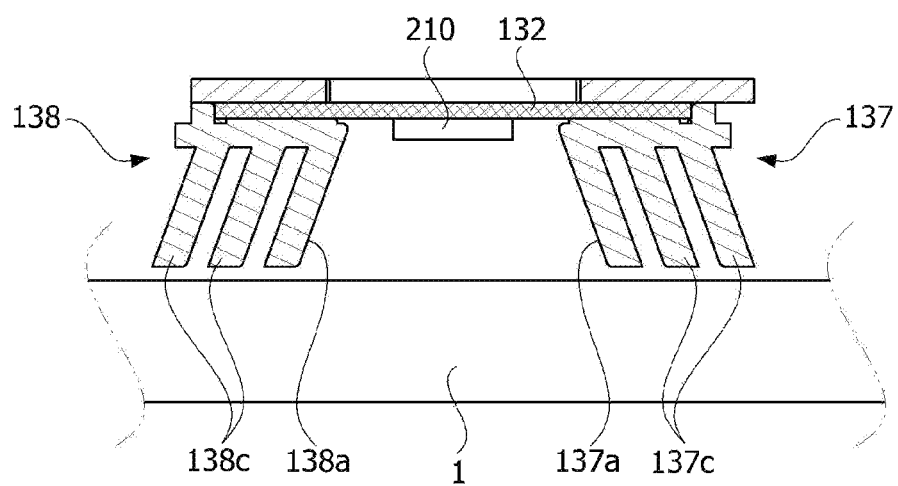

[FIG. 19]
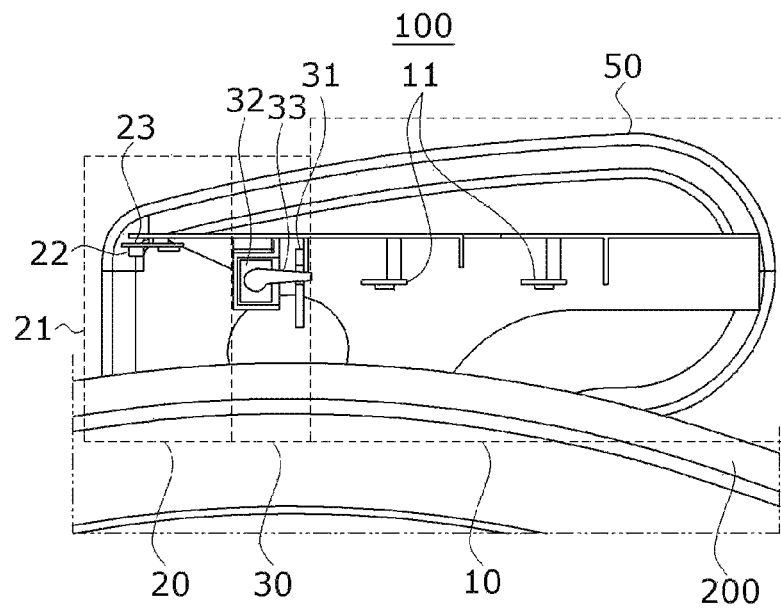
[FIG. 20]
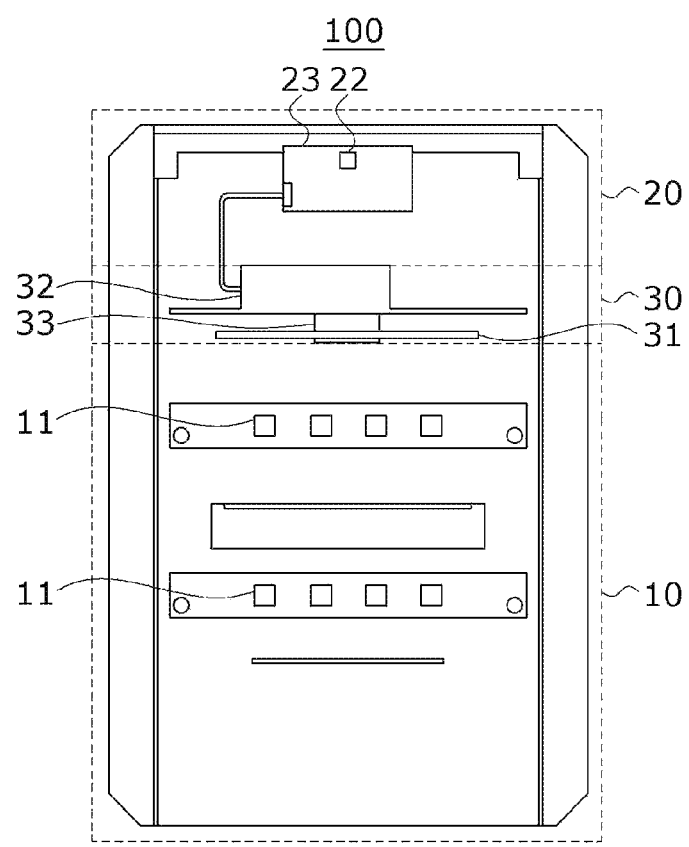

【FIG. 21】
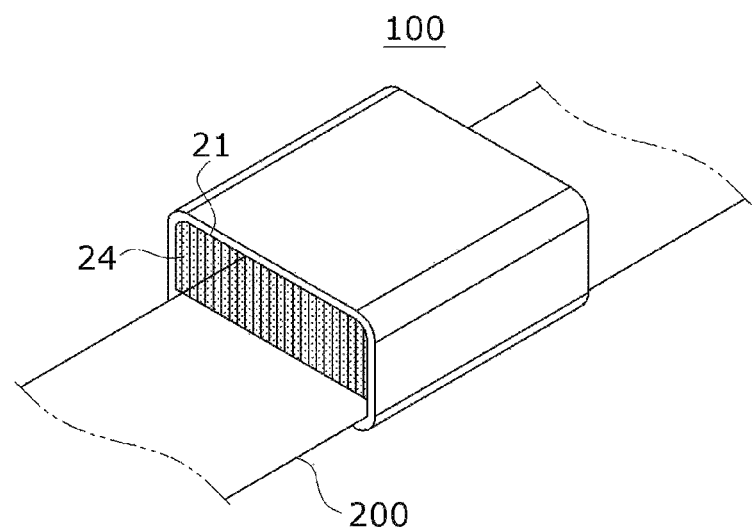
【FIG. 22】
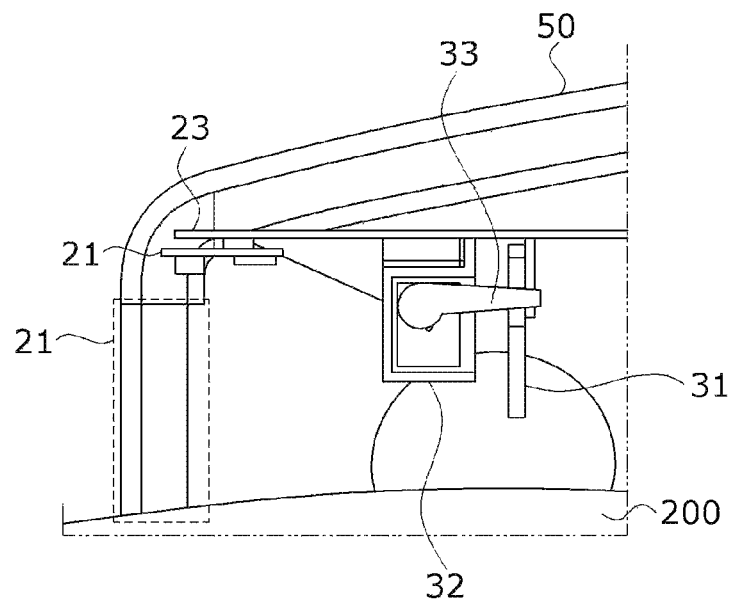

【FIG. 23】
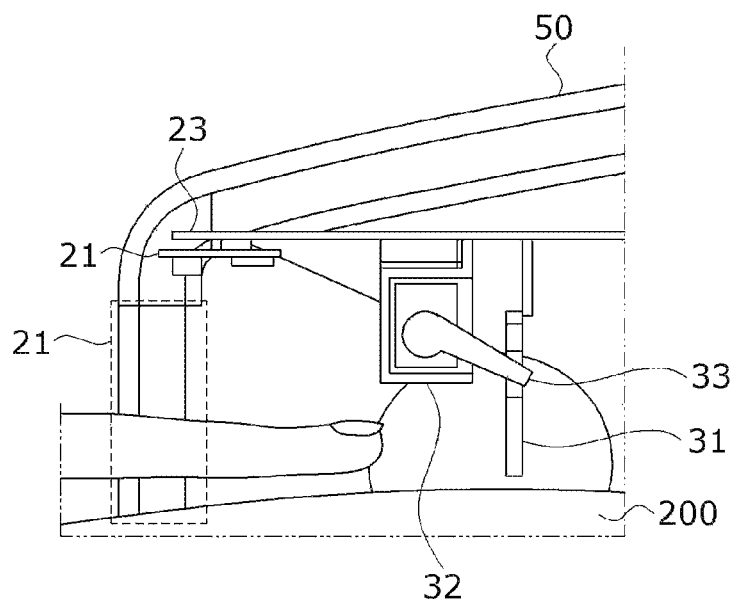
【FIG. 24】
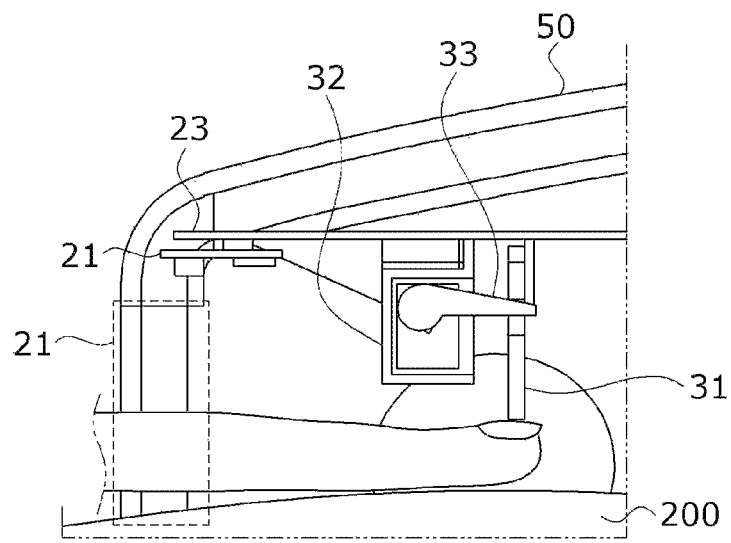

[FIG. 25]
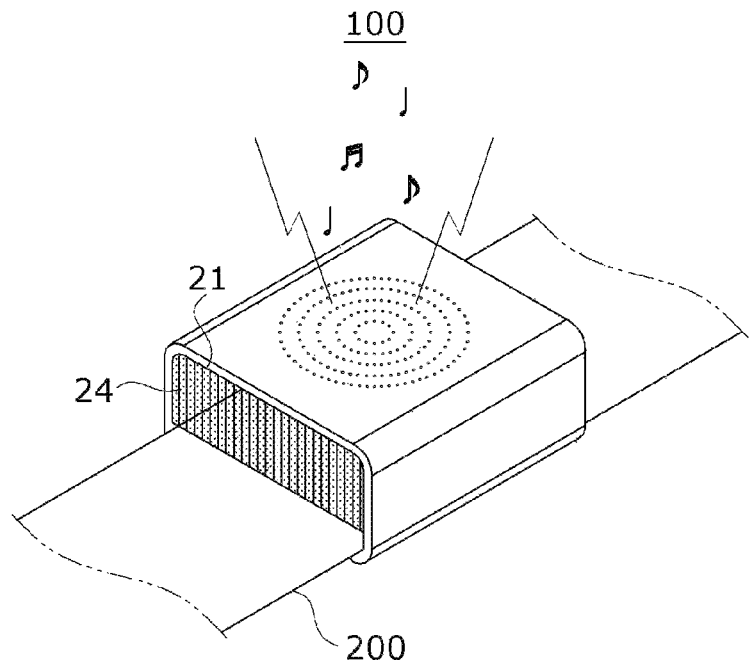
[FIG. 26]
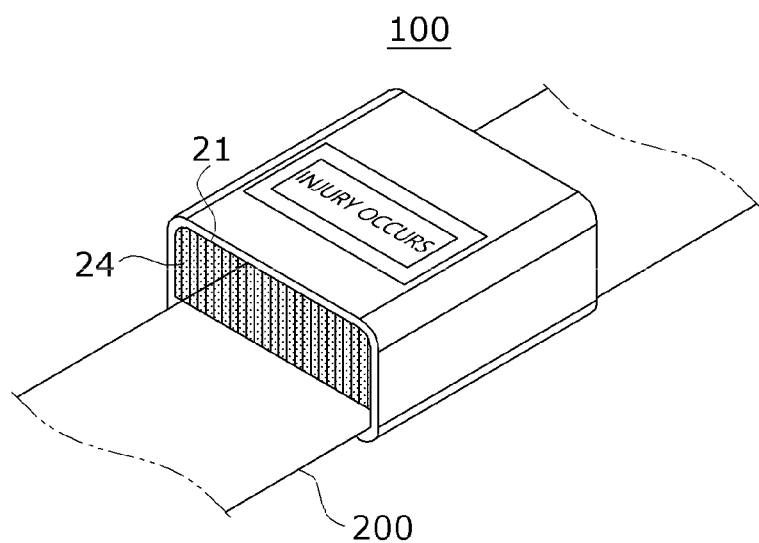

LIGHT SOURCE APPARATUS

CROSS REFERENCE TO RELATED APPLICATIONS

This application is the National Phase of PCT International Application No. PCT/KR2018/015461, filed on Dec. 7, 2018, which claims priority under 35 U.S.C. 119(a) to Patent Application Nos. 10-2017-0167538, filed in the Republic of Korea on Dec. 7, 2017; 10-2017-0181923, filed in the Republic of Korea on Dec. 28, 2017; and 10-2017-0181924, filed in the Republic of Korea on Dec. 28, 2017, all of which are hereby expressly incorporated by reference into the present application.

TECHNICAL FIELD

An embodiment relates to a light source apparatus.

BACKGROUND ART

An escalator and a moving walkway are installed in various places, such as subways, airports, and department stores, having many floating populations and convenient for many people. However, a handrail which is a safety device for an escalator and a moving walkway is easily exposed to bacteria.

Recently, a device for sterilizing a hand rail using an ultraviolet light emitting device has been developed. The ultraviolet light emitting device can output light (ultraviolet (UV)-A) in a near ultraviolet wavelength range, can output light (UV-B) in a far ultraviolet wavelength range, and can output light (UV-C) in a deep ultraviolet wavelength range. Among the above, the light (UV-C) in the deep ultraviolet wavelength range can have a sterilizing function.

The ultraviolet light emitting device can increase a sterilization effect when uniformly irradiated onto the hand rail. However, since the hand rail has various sizes and shapes, there is a problem in that the sterilization effect is not guaranteed according to types of the hand rail to be mounted.

Further, there is a risk that a safety accident can occur when a user' hand or foreign substances are introduced into a sterilization device.

In addition, since the user generally moves by holding the hand rail, side surfaces of the hand rail can be easily exposed to bacteria. Accordingly, it is necessary to sterilize the side surfaces of the hand rail.

SUMMARY

An embodiment is directed to providing a light source apparatus capable of simultaneously performing ultraviolet sterilization and heat sterilization on a hand rail.

An embodiment is directed to providing a light source apparatus capable of adjusting a position of a light source module according to the type of hand rail.

An embodiment is directed to providing a light source apparatus capable of preventing the introduction of a user's hand or foreign substances.

An embodiment is directed to providing a light source apparatus capable of also sterilizing side surfaces of a hand rail.

Problems desired to be solved by the embodiment are not limited thereto-described problems, and objects and effects understood from solutions and embodiments which will be described below are also included.

One aspect of the present invention provides a light source apparatus including: a housing; a coupling unit configured to fix the housing to a target structure; a light source module configured to emit light onto the target structure; and a power source module configured to supply electrical power to the light source module, wherein the light source module includes a first circuit board, a second circuit board disposed at one side of the first circuit board, a third circuit board disposed at the other side of the first circuit board, at least one first ultraviolet light emitting element disposed on one surface of the first circuit board, at least one second ultraviolet light emitting element disposed on one surface of the second circuit board, and at least one third ultraviolet light emitting element disposed on one surface of the third circuit board, and the one surface of the second circuit board and the one surface of the third circuit board are disposed to face each other.

The light source apparatus may include a first connector configured to connect the first circuit board and the second circuit board and a second connector configured to connect the first circuit board and the third circuit board.

The second ultraviolet light emitting element and the third ultraviolet light emitting element may emit ultraviolet light onto side surfaces of the target structure.

The light source module may include a heat dissipation plate disposed on the first circuit board, the heat dissipation plate may include at least one or more cavities, the at least one first ultraviolet light emitting element may be disposed in the cavity, the heat dissipation plate may include a first heat dissipation plate and a second heat dissipation plate which are disposed to be spaced apart from each other, the first heat dissipation plate may include a first inclined surface, the second heat dissipation plate may include a second inclined surface facing the first inclined surface, and an interval between the first inclined surface and the second inclined surface may increase as the distance from the first circuit board increases.

The first heat dissipation plate may include a plurality of first heat dissipation fins connected to the first inclined surface, the second heat dissipation plate may include a plurality of second heat dissipation fins connected to the second inclined surface, and the plurality of first heat dissipation fins and the plurality of second heat dissipation fins may be disposed in parallel with the first circuit board.

The first heat dissipation plate may include a plurality of first heat dissipation fins protruding toward the target structure, the second heat dissipation plate may include a plurality of second heat dissipation fins protruding toward the target structure, each of the plurality of first heat dissipation fins may have the same inclination angle as the first inclined surface, each of the plurality of second heat dissipation fins may have the same inclination angle as the second inclined surface, and a minimum interval between the target structure and the first heat dissipation plate may be smaller than a minimum interval between the target structure and the first ultraviolet light emitting element.

The light source apparatus may include a support frame coupled to the first to third circuit boards, wherein the support frame may include a support plate to which the first to third circuit boards are fixed, a fixing plate configured to fix the support plate to the housing, and a connection part configured to connect the support plate and the fixing plate, the fixing plate may include a first hole coupled to a screw, and the first hole may extend in a first direction.

The support plate may include a first hole disposed in a region where the first circuit board is fixed, and the light source module may include a third heat dissipation plate thermally connected to the first circuit board through the first hole.

The light source module may include a support frame configured to fix the first to third circuit boards to the housing, and a position adjusting part configured to adjust a position where the support frame is fixed to the housing.

The housing may include an inlet and an outlet through which a rotating rail of the target structure passes, a first brush disposed at the inlet of the housing, and a second brush disposed at the outlet of the housing, the first brush may include a second hole coupled to the housing by a screw, the second brush may include a third hole coupled to the housing by a screw, and the second hole and the third hole may be formed to extend in a vertical direction.

The light source apparatus may include a sensing part disposed adjacent to the light source module, and a blocking part disposed between the light source module and the sensing part, wherein the sensing part may include an opening configured to open some region of the sensing part to the outside, and a sensing element disposed at the opening to generate a sensing signal which senses the entry and exit of an object, the blocking part may include a safety shield configured to block the sensing part and the light source module, and the safety shield may be driven in response to the sensing signal generated from the sensing element.

The first circuit board may include heat conductive pad portions disposed at both sides thereof in a first direction which is an extending direction of the first circuit board, a circuit pattern electrically connected to the at least one ultraviolet light emitting element, and an insulation layer disposed on the circuit pattern, the heat conductive pad portions may be coplanarly disposed with the circuit pattern, and the first heat dissipation plate and the second heat dissipation plate may come into contact with the heat conductive pad portions.

The target structure may include a hand rail, and the housing may include an inlet and an outlet through which a rotating rail of the target structure passes.

The power source module may include a roller rotated by the hand rail, and a power supply rotated by the roller to generate power.

The roller and the power supply may be disposed in a direction from the inlet toward the outlet, and the roller may be disposed farther from the inlet than the power supply.

The light source apparatus may include an elastic member configured to connect the power source module to the housing, wherein the elastic member may restore the roller to an original position when the roller is spaced apart from the rotating rail.

The light source apparatus may include a case disposed on the housing.

An angle formed by a first direction which is an extending direction of the first circuit board and a second direction which is an extending direction of the second circuit board may be smaller than 180°.

The light source module may emit the ultraviolet light onto an upper surface and side surfaces of the target structure to perform sterilization.

Each of the first brush and the second brush may be formed of an elastic material.

Advantageous Effects

According to the present invention, sterilizing power can be improved by simultaneously applying ultraviolet sterilization and heat sterilization to a hand rail.

Further, a sterilization effect can be improved by adjusting a position of a light source module according to the type of the hand rail.

In addition, the introduction of a user's hand or foreign substances into a light source apparatus can be prevented.

In addition, sterilizing power can be improved by also sterilizing side surfaces of the hand rail.

In addition, even when a passenger places his/her hand on an escalator rail, since the light source apparatus detects this and thus a safety shield descends before the hand is suctioned into the inside, a personal injury can be prevented.

In addition, when the light source apparatus senses a passenger's hand, since the light emitting element is turned off, an adverse effect on the human body in the case of the light emitting element being an ultraviolet (UV) LED can be fundamentally blocked.

In addition, when the light source apparatus senses a passenger's hand, since signals which stop the driving of the escalator are generated, additional injury can be prevented.

Various useful advantages and effects of the present invention are not limited thereto and may be understood relatively easily in the course of describing exemplary embodiments of the present invention.

BRIEF DESCRIPTION OF THE DRAWINGS

FIG. 1 is a view illustrating a state in which a light source apparatus according to one embodiment of the present invention is mounted on a target structure.

FIG. 2 is a perspective view of the light source apparatus according to one embodiment of the present invention.

FIG. 3 is a front view of the light source apparatus according to one embodiment of the present invention.

FIG. 4 is a view in which a housing and a case are separated.

FIG. 5 is a cross-sectional view in direction A-A of FIG. 3.

FIG. 6 is a view illustrating a structure of a power source module.

FIG. 7A is a view illustrating a state in which a first brush and a second brush are fixed to the housing.

FIG. 7B is a view illustrating a process of adjusting a fixing position of the first brush.

FIG. 7C is a view illustrating a process of adjusting a fixing position of the second brush.

FIG. 8 is an exploded perspective view of the light source module.

FIG. 9 is a view illustrating a state in which the light source module is fixed to the housing.

FIG. 10 is a view illustrating a state in which the light source module emits ultraviolet light onto the hand rail.

FIGS. 11 and 12 are views illustrating a process of adjusting a position of the light source module.

FIG. 13 is a conceptual diagram illustrating a process in which the light source module applies ultraviolet light and heat to the hand rail.

FIG. 14 is a front view of the light source module according to one embodiment of the present invention.

FIG. 15 is a cross-sectional view in direction B-B of FIG. 14.

FIG. 16 is a view illustrating a coupling relation between a heat dissipation plate and a circuit board.

FIG. 17 is an enlarged view of portion A in FIG. 15.

FIG. 18 is a modified example of FIG. 17.

FIG. 19 is a view illustrating a side perspective view of a light source apparatus according to another embodiment of the present invention.

FIG. 20 is a view illustrating a cross-sectional perspective view of the light source apparatus according to another embodiment of the present invention.

FIG. 21 is a view illustrating a case in which a blocking shield is installed in an opening.

FIG. 22 is a view illustrating a normal state of the light source apparatus according to another embodiment of the present invention.

FIG. 23 is a view illustrating a state in which a passenger's hand is suctioned through the opening of the light source apparatus according to another embodiment of the present invention.

FIG. 24 is a view illustrating a state in which a passenger's hand is caught between the safety shield and a rail of an escalator.

FIGS. 25 and 26 are views illustrating a case in which notification signals are output through a notification part.

DETAILED DESCRIPTION

The embodiments may be modified into other forms or some of the embodiments may be combined, and the scope of the present invention is not limited to embodiments which will be described below.

Although items described in a specific embodiment are not described in another embodiment, the items may be understood as a description related to the other embodiment unless a description contrary to or contradicting the items is in the other embodiment.

For example, when a characteristic of a component A is described in a specific embodiment and a characteristic of a component B is described in another embodiment, the characteristics of the components are understood to fall within the scope of the present invention unless a contrary or contradictory description is present even when an embodiment in which the component A and the component B are combined is not clearly disclosed.

In the description of the embodiments, when one element is disclosed to be formed "on or under" another element, the term "on or under" includes both a case in which the two elements are in direct contact with each other and a case in which at least another element is disposed between the two elements (indirect contact). Further, when the term "on or under" is expressed, a meaning of not only an upward direction but also a downward direction with respect to one element may be included.

Hereinafter, embodiments of the present invention will be described in detail with reference to the accompanying drawings so that those skilled in the art may easily carry out the embodiment of the present invention.

FIG. 1 is a view illustrating a state in which a light source apparatus according to one embodiment of the present invention is mounted on a target structure, FIG. 2 is a perspective view of the light source apparatus according to one embodiment of the present invention, FIG. 3 is a front view of the light source apparatus according to one embodiment of the present invention, and FIG. 4 is a view in which a housing and a case are separated.

Referring to FIGS. 1 and 2, a light source apparatus 100 according to one embodiment of the present invention may be mounted on the target structure to sterilize a surface of a rail 1 of a target structure 2. The target structure 2 may include all various structures, such as an escalator and a moving walkway, which move users to a determined position. The rail 1 of the target structure may be a hand rail of the escalator or moving walkway, but is not limited thereto. Hereinafter, the surface of the target structure will be described as the hand rail.

The light source apparatus 100 may include a front case 111 in which a window 111a which outputs information related to sterilization is disposed, and a side case 112 which extends from the front case 111 to be mounted on the target structure. The side case 112 may have a triangular shape in which the farther from the front, the narrower the width, but is not limited thereto.

Referring to FIG. 3, a coupling unit 120 disposed in the case 110 may include first and second coupling plates 121 and 122. The coupling unit 120 may adjust an interval G1 between the first and second coupling plates 121 and 122 to be fixed to the target structure. A structure by which the coupling unit 120 is fixed to the target structure is not particularly limited.

Referring to FIG. 4, the case 110 may be coupled to a housing 113 to form an exterior. The case 110 may include a plastic material, but is not limited thereto. The housing 113 may include a front surface portion 113a, an upper surface portion 113c, and a side surface portion 113b.

FIG. 5 is a cross-sectional view in direction A-A of FIG. 3, FIG. 6 is a view illustrating a structure of a power source module, FIG. 7A is a view illustrating a state in which a first brush and a second brush are fixed to the housing, FIG. 7B is a view illustrating a process of adjusting a fixing position of the first brush, and FIG. 7C is a view illustrating a process of adjusting a fixing position of the second brush.

Referring to FIG. 5, the light source apparatus 100 according to the embodiment may include the coupling unit 120 which fixes the housing 113 to the target structure, a light source module 130 which emits ultraviolet light onto the hand rail 1, and a power source module 140 which supplies electrical power to the light source module 130. The light source module 130 may be disposed to be inclined by a predetermined angle θ1 from a vertical direction of the housing 113.

The housing 113 may accommodate the light source module 130 and the power source module 140. A shape or material of the housing 113 is not particularly limited. A display part 160 which displays a current state of the light source apparatus may be disposed at an upper portion of the housing 113. The display part 160 may include a separate liquid crystal panel or light emitting diodes with various colors capable of displaying states.

The housing 113 may include an inlet E1 and an outlet E2 through which the hand rail 1 of the target structure passes. The hand rail 1 may continuously pass through the inside of the housing 113 through the inlet E1 and the outlet E2.

A first brush 152 may be disposed at the inlet E1 of the housing 113 to prevent the introduction of a user's hand or foreign substances into the light source apparatus, and a second brush 151 may be disposed at the outlet E2 of the housing 113 to prevent the introduction of the user's hand or foreign substances into the light source apparatus.

The light source module 130 may sterilize the hand rail 1 by emitting the ultraviolet light onto the hand rail 1. Ultraviolet light emitting elements 210 and 220 may output light (ultraviolet (UV)-A) in a near ultraviolet wavelength range, may output light (UV-B) in a far ultraviolet wavelength range, and may output light (UV-C) in a deep ultraviolet wavelength range. A wavelength range may be determined by a composition ratio of Al in a semiconductor structure.

For example, the light (UV-A) in the near ultraviolet wavelength range may have a main peak in a range of 320 nm to 420 nm, the light (UV-B) in the far ultraviolet wavelength range may have a main peak in a range of 280 nm to 320 nm, and the light (UV-C) in the deep ultraviolet wavelength range may have a main peak in a range of 100 nm to 280 nm.

The power source module 140 may rotate with the hand rail 1 to generate electrical power. The generated electrical power may drive the ultraviolet light emitting elements of the light source module 130.

Referring to FIG. 6, the power source module 140 may include a roller 141 which comes into contact with the hand rail 1 and a power supply 142 which rotates due to the roller 141 to generate electrical power. The roller 141 and the power supply 142 may be connected to each other by a gear (not shown). The power supply 142 may include all various self-generator structures capable of converting a rotational force of the roller 141 into electrical power.

The power source module 140 may directly supply the electrical power generated from the power supply 142 to the light source module 130 but is not limited thereto. For example, the power source module 140 may store some of the generated electrical power in a battery (not shown). Accordingly, the electrical power stored in the battery may be used when necessary.

The roller 141 and the power supply 142 may be disposed in a direction from the inlet E1 to the outlet E2, and the roller 141 may be disposed farther away from the inlet E1 than the power supply 142. That is, the roller 141 may be disposed closer to the light source module 130 than the power supply 142. According to this configuration, the roller 141 may be disposed relatively distant to prevent a problem of a user's hand being introduced into the light source apparatus by the roller 141.

The power source module 140 may include an elastic member 143 connected to the housing 113. The elastic member 143 may connect the power source module 140 to the inlet E1 of the housing 113. The elastic member 143 may have an elastic force so that the roller 141 may come into contact with the hand rail 1. Accordingly, the elastic member 143 may bring the roller 141 into contact with an upper surface of the hand rail 1. According to the embodiment, a position of the power supply 142 may be disposed a predetermined interval dl higher than a position where the roller 141 comes into contact with the hand rail 1 to be spaced apart from the hand rail 1.

Referring to FIGS. 7A and 7B, the first brush 152 may be disposed at the inlet E1 of the housing 113 to prevent the introduction of a user's hand or foreign substances into the light source apparatus. A second hole 152a of the first brush 152 may be coupled to a second screw S2 to fix the first brush 152 to the housing 113.

In this case, the second hole 152a may be formed to extend in a vertical direction D1 to move the first brush 152 in the vertical direction D1. Here, the vertical direction is a direction closer to and farther from the hand rail. According to the embodiment, the second screw S2 may be coupled and fixed to the second hole 152a after moving and adjusting the first brush 152 in a vertical direction so that the first brush 152 has a first separation distance G2 from the hand rail 1. The first separation distance G2 may be 5 mm to 15 cm, but is not limited thereto.

Referring to FIGS. 7A and 7C, the second brush 151 may be disposed at the outlet E2 of the housing 113 to prevent the introduction of a user's hand or foreign substances into the light source apparatus. A third hole 151a of the second brush 151 may be coupled to a third screw S3 to fix the second brush 151 to the housing 113.

In this case, the third hole 151a may be formed to extend in the vertical direction D1 to move the second brush 151 in the vertical direction D1. That is, the third screw S3 may be coupled and fixed to the third hole 151a after disposing the second brush 151 so that the second brush 151 has a second separation distance G3 from the hand rail 1. The second separation distance G3 may be 5 mm to 15 cm, but is not limited thereto.

An extending direction of the third hole 151a may cross an extending direction of a first hole 131b-1 which fixes the light source module 130 to the housing. That is, the third hole 151a may extend in the vertical direction to move the second brush 151 in the vertical direction, but the first hole 131b-1 may extend in a horizontal direction to move the light source module 130 in the horizontal direction. Accordingly, the extending direction of the third hole 151a and the extending direction of the first hole 131b-1 may be disposed to be perpendicular to each other.

Types of the first brush 152 and the second brush 151 are not particularly limited as long they are made of an elastic material. When the first brush 152 and the second brush 151 have high strength, a user's hand may be hurt when caught. Further, when the hand rail 1 collides with the first and second brushes 152 and 151, an impact may be applied to the light source apparatus. For example, the first brush 152 and the second brush 151 may be formed of a silicon material.

FIG. 8 is an exploded perspective view of the light source module, FIG. 9 is a view illustrating a state in which the light source module is fixed to the housing, FIG. 10 is a view illustrating a state in which the light source module emits ultraviolet light onto the hand rail, and FIGS. 11 and 12 are views illustrating a process of adjusting a position of the light source module.

Referring to FIG. 8, the light source module 130 may include a first circuit board 132, a second circuit board 133 disposed at one side of the first circuit board 132, and a third circuit board 134 disposed at the other side of the first circuit board 132. In this case, one surface of the second circuit board 133 and one surface of the third circuit board 134 may be disposed to face each other.

At least one first ultraviolet light emitting element 210 may be disposed on one surface 132a of the first circuit board 132. For example, the number of first ultraviolet light emitting elements 210 which are disposed may be three, but is not limited thereto. Further, at least one second ultraviolet light emitting element 220 may be disposed on one surface of the second circuit board 133, and at least one third ultraviolet light emitting element 230 may be disposed on one surface of the third circuit board 134.

In this case, the one surface of the second circuit board 133 and the one surface of the third circuit board 134 may be disposed to face each other with the target structure therebetween. Accordingly, the second ultraviolet light emitting element 220 and the third ultraviolet light emitting element 230 may also be disposed to face each other and emit the ultraviolet light onto side surfaces of the hand rail 1.

The second circuit board 133 may be disposed to be inclined by a predetermined angle from the first circuit board 132. Accordingly, a first direction (an X axis direction) which is a longitudinal direction of the first circuit board 132 and a second direction (a Y axis direction) which is a longitudinal direction of the second circuit board 133 may have an angle smaller than 180°. In the drawing, an example in which the first direction and the second direction are perpendicular to each other is described, but is not limited thereto. Further, the third circuit board 134 may also be inclined by a predetermined angle from the other side of the first circuit board 132.

The first circuit board 132 and the second circuit board 133 may be electrically connected to each other by a first connector 135*a*. That is, when electrical power is input to the first circuit board 132, the electrical power may also be applied to the second circuit board 133 through the first connector 135*a*. Like the above, the first circuit board 132 and the third circuit board 134 may be electrically connected to each other by a second connector 135*b*.

A heat dissipation plate 136 is disposed on one surface of the first circuit board 132, and may include at least one or more cavities C1 therein. The at least one first ultraviolet light emitting element 210 may be disposed in the cavity C1.

Specifically, the heat dissipation plate 136 may include a first heat dissipation plate 137 and a second heat dissipation plate 138 which are spaced apart from each other. The cavity C1 may be an interval between the first heat dissipation plate 137 and the second heat dissipation plate 138.

The first heat dissipation plate 137 and the second heat dissipation plate 138 may extend in the longitudinal direction of the first circuit board 132, and the at least one first ultraviolet light emitting element 210 may be disposed between the first heat dissipation plate 137 and the second heat dissipation plate 138. Accordingly, heat generated from the first ultraviolet light emitting element 210 may be quickly dissipated through the first heat dissipation plate 137 and the second heat dissipation plate 138. The light emitting elements according to the embodiment are ultraviolet light emitting elements and thus may generate relatively more heat than a visible light emitting element. Accordingly, it may be important that the heat should be quickly dissipated.

A support frame 131 may be coupled to the first to third circuit boards 132, 133, and 134. The support frame 131 may include support plates 131*a*, 131*d*, and 131*c* to which the first to third circuit boards 132, 133, and 134 are fixed, a fixing plate 131*b* which fixes the support plates 131*a*, 131*d*, and 131*c* to the housing 113, and a connection part 131*f* which connects the support plates 131*a*, 131*d*, and 131*c* and the fixing plate 131*b*.

The support plates 131*a*, 131*d*, and 131*c* may include a first support plate 131*a* to which the first circuit board 132 is fixed, a second support plate 131*d* to which the second circuit board 133 is fixed, and a third support plate 131*c* to which the third circuit board 134 is fixed.

The fixing plate 131*b* may be connected to the first support plate 131*a* through the connection part 131*f*. The fixing plate 131*b* may be vertically bent with respect to the first support plate 131*a*. The first hole 131*b*-1 formed in the fixing plate 131*b* may extend in the first direction (the X axis direction) which is the longitudinal direction of the first circuit board 132.

A protruding portion 131*g* may be vertically bent with respect to the fixing plate 131*b*. Accordingly, the protruding portion 131*g* may be disposed in parallel with the first support plate 131*a*.

The first support plate 131*a* may include an opening 131*e* formed in a region where the first circuit board 132 is fixed. A third heat dissipation plate 139 may come into contact with the other surface of the first circuit board 132 through the opening 131*e*. Accordingly, a heat dissipation effect may be improved.

Referring to FIGS. 9 and 10, the fixing plate 131*b* of the support frame may be fixed to the front surface portion 113*a* of the housing 113, and the protruding portion 131*g* of the support frame may be inserted into a guide hole 113*a*-1 of the housing 113.

The light source module 130 may emit the ultraviolet light onto the hand rail 1 to sterilize the surfaces of the hand rail 1. The light source module 130 may emit light onto a three-dimensional surface (topology) of the target structure. When the emitted light is an ultraviolet ray, the surfaces of the hand rail 1 may be sterilized. Since the second circuit board 133 and the third circuit board 134 are disposed to face each other, the second ultraviolet light emitting element 220 and the third ultraviolet light emitting element 230 may also sterilize the side surfaces of the hand rail 1.

Generally, the user holds the hand rail 1 by hand and thus comes into contact with not only the upper surface but also the side surfaces of the hand rail 1. Accordingly, when the side surfaces of the hand rail 1 are also sterilized, the sterilization effect may be further improved.

In this case, when the ultraviolet light emitting elements uniformly emit the light onto the area of the hand rail 1, the sterilization effect may be improved. However, since the hand rail 1 has various shapes and sizes, a position of the light source module 130 has to be adjusted according to the type of the hand rail 1.

The light source module 130 may include a position adjusting part 131*h* which adjusts a position where the fixing plate 131*b* is fixed to the housing 113. The position adjusting part 131*h* may include at least one first hole 131*b*-1 and first screw S1.

The first hole 131*b*-1 may extend in the first direction (the X axis direction) which is the longitudinal direction of the first circuit board 132. Accordingly, since the light source module 130 is moved to a desired position along the longitudinal direction of the first circuit board 132 and the first screw S1 is coupled to the light source module 130, the position where the light source module 130 is fixed to the housing 113 may be adjusted.

In this case, since the protruding portion 131*g* of the support frame is inserted into the guide hole 113*a*-1 of the housing 113, the light source module 130 may be held on the front surface portion 113*a* of the housing even before coupling the first screw S1 to the first hole 131*b*-1. Accordingly, the position where the light source module 130 is mounted may be easily and accurately adjusted.

Referring to FIG. 11, when the support frame 131 is disposed eccentrically to the right (W1) in comparison with the hand rail 1, since the ultraviolet light is not uniformly emitted to the area of the hand rail 1, the sterilization effect may be degraded. Further, since a distance between the third ultraviolet light emitting element 230 and the hand rail 1 increases, a side sterilization effect may also be degraded.

In this case, a center may be aligned by moving the support frame 131 to the left based on the drawing. The first hole 131*b*-1 and the guide hole 113*a*-1 are formed to extend in a longitudinal direction and thus the support frame 131 may be moved to the left as much as desired.

In the case of FIG. 12, since the support frame 131 is disposed eccentrically to the left (W2) in comparison with the hand rail 1, and thus the ultraviolet light is not uniformly emitted to the area of the hand rail 1, the sterilization effect may be degraded. In this case, a center may be aligned by moving the support frame 131 to the right based on the drawing.

FIG. 13 is a conceptual diagram illustrating a process in which the light source module applies ultraviolet light and heat to the hand rail, FIG. 14 is a front view of the light source module according to one embodiment of the present invention, FIG. 15 is a cross-sectional view in direction B-B of FIG. 14, FIG. 16 is a view illustrating a coupling relation between an heat dissipation plate and a circuit board, FIG. 17 is an enlarged view of portion A in FIG. 15, and FIG. 18 is a modified example of FIG. 17.

Referring to FIG. 13, since a plurality of first ultraviolet light emitting elements 210 disposed on one surface of the first circuit board 132 emit light onto the upper surface of the hand rail 1, and the second ultraviolet light emitting element 220 disposed on the second circuit board 133 and the third ultraviolet light emitting element 230 disposed on the third circuit board 134 emit light onto the side surfaces of the hand rail 1, the hand rail 1 may be sterilized.

The heat dissipation plate 136 may include at least one cavity C1 in which the first ultraviolet light emitting elements 210 are disposed. Accordingly, a directional angle of the light emitted from the first ultraviolet light emitting elements 210 may be controlled. The heat dissipation plate 136 may be disposed only on the first circuit board 132, but is not limited thereto, and may also be disposed on the second circuit board 133 and the third circuit board 134 to also control a directional angle of the light emitted from each of the second ultraviolet light emitting element 220 and the third ultraviolet light emitting element 230.

Further, the heat dissipation plate 136 may dry the hand rail 1 using heat generated from the first to third ultraviolet light emitting elements 210, 220, and 230. Accordingly, the sterilization effect of the hand rail 1 may be improved.

The heat dissipation plate 136 may be disposed to face the hand rail 1 at an inner side of the circuit board to perform a heat sterilization function. In this case, a third separation distance d3 between the heat dissipation plate 136 and the hand rail 1 may be 5 mm to 15 cm. When the third separation distance between the heat dissipation plate 136 and the hand rail 1 is 5 mm or more, the heat dissipation plate 136 may be prevented from contact with the hand rail 1 by securing a sufficient separation distance, and when the third separation distance d3 is 15 cm or less, the heat dissipation plate 136 may be disposed close enough to dry the hand rail 1 using the heat emitted from the heat dissipation plate 136.

Referring to FIGS. 14 and 15, the heat dissipation plate 136 may include a first heat dissipation plate 137 and a second heat dissipation plate 138 which are spaced apart from each other. The cavity C1 may be an interval between the first heat dissipation plate 137 and the second heat dissipation plate 138.

The first heat dissipation plate 137 and the second heat dissipation plate 138 extend in the longitudinal direction of the first circuit board 132, and the at least one first ultraviolet light emitting element 210 may be disposed between the first heat dissipation plate 137 and the second heat dissipation plate 138.

The third separation distance d3 between the hand rail 1 and the first and second heat dissipation plates 137 and 138 may be smaller than a separation distance between the hand rail 1 and the first ultraviolet light emitting element 210. Accordingly, the hand rail 1 may be sterilized by the ultraviolet light and dried by the heat emitted from the first and second heat dissipation plates 137 and 138, at the same time.

In this case, a first inclined surface 137a of the first heat dissipation plate 137 and a second inclined surface 138a of the second heat dissipation plate 138 may be disposed to face each other. Accordingly, the first inclined surface 137a and the second inclined surface 138a may form sidewalls of the cavity C1. In this case, an interval between the first inclined surface 137a and the second inclined surface 138a may increase the further away from the first circuit board 132. Accordingly, since the directional angle of the light emitted from the first ultraviolet light emitting element 210 is controlled by the first inclined surface 137a and the second inclined surface 138a, the ultraviolet light may be uniformly emitted to the hand rail 1. An angle (an inclination angle of the cavity) between the first inclined surface 137a and the second inclined surface 138a may be 20° to 60°, but is not limited thereto.

Referring to FIG. 16, the first circuit board 132 may include heat conductive pad portions 132e disposed at both sides in the longitudinal direction, a circuit pattern 132d electrically connected to the at least one first ultraviolet light emitting element 210, and an insulation layer 132c which covers the circuit pattern 132d.

In the first circuit board 132, the heat conductive pad portions 132e may be formed by leaving some conductive layers at both sides in the longitudinal direction in a process of forming the circuit pattern 132d on the substrate. That is, the heat conductive pad portions 132e may be coplanarly disposed with the circuit pattern 132d. In this case, the heat conductive pad portions 132e may be connected to the first ultraviolet light emitting element 210. Accordingly, the heat from the first ultraviolet light emitting element 210 may be quickly transferred to the first and second heat dissipation plates 137 and 138 through the heat conductive pad portions 132e.

Referring to FIG. 17, the first heat dissipation plate 137 may include the first inclined surface 137a, and the second heat dissipation plate 138 may include the second inclined surface 138a facing the first inclined surface 137a. In this case, the first inclined surface 137a and the second inclined surface 138a have a reflectivity like a mirror through the front post-processing. Accordingly, the efficiency of emitting the ultraviolet light onto the hand rail 1 may be improved.

In this case, the first heat dissipation plate 137 may include a plurality of first heat dissipation fins 137b connected to the first inclined surface 137a, and the second heat dissipation plate 138 may include a plurality of second heat dissipation fins 138b connected to the second inclined surface 138a. Accordingly, the heat from the ultraviolet light emitting elements may be quickly dissipated through the first and second heat dissipation fins 137a and 138a and the hand rail 1 may be thermally sterilized.

In this case, the plurality of first heat dissipation fins 137b and the plurality of second heat dissipation fins 138b may be disposed in parallel with the first circuit board 132, but are not limited thereto. For example, as shown in FIG. 18, the first heat dissipation plate 137 may include a plurality of first heat dissipation fins 137c protruding toward the hand rail 1, and the second heat dissipation plate 138 may include a plurality of second heat dissipation fins 138c protruding toward the hand rail 1.

In this case, each of the plurality of first heat dissipation fins 137c may have the same inclination angle as the first inclined surface 137a, and each of the plurality of second heat dissipation fins 138c may have the same inclination angle as the second inclined surface 138a. According to this configuration, the heat emitted from spaces between the heat dissipation fins dries the hand rail 1, and thus the sterilization effect may be enhanced.

FIG. 19 is a view illustrating a side perspective view of a light source apparatus 100 according to another embodiment of the present invention, and FIG. 20 is a view illustrating a cross-sectional perspective view.

The light source apparatus 100 according to the embodiment of the present invention may include a light source part (a light source module 10), a sensing part 20, and a blocking part 30, the sensing part 20 may include an opening 21 and a sensing element 22, and the blocking part 30 may include a safety shield 31.

Further, the light source apparatus 100 according to the embodiment of the present invention may include not only the above-described components but also all other additional components required to achieve the purposes of the present invention. For example, the light source apparatus 100 according to the embodiment of the present invention may further include a cover part 50 which prevents exposure of the above-described components which are installed therein to the outside.

Meanwhile, the light source apparatus 100 according to the embodiment of the present invention may be mainly installed on a rail 200 of the escalator to sterilize the rail 200, but is not limited thereto, and since the light source apparatus 100 is implemented to have partially different sizes and other components, it may be installed on not only the rail 200 of the escalator but also other public facilities to perform sterilization work. Hereinafter, the light source part 10 will be described first.

The light source part 10 includes a plurality of light emitting elements 11. The light source part 10 may include all components of the above-described light source module.

Here, one or more of the plurality of light emitting elements 11 may be an UV light emitting diode (LED), and accordingly, the surfaces of the rail 200 of the escalator may be sterilized.

Here, the plurality of light emitting elements 11 may be turned on or turned off in response to sensing signals generated by the sensing element 22 which will be described later. For example, when the sensing element 22 senses a passenger's hand, the light emitting elements 11 may be turned off not to emit light of a wavelength which is harmful to the passenger's hand, and may perform the sterilization work of the escalator rail 200 in only a safe state in which the passenger's hand is not sensed.

Since the light emitting elements 11 may be disposed in plural at a predetermined height from the escalator rail 200, here, a disposition height and a disposition number may be set in consideration of a light emitting area which may be covered by each of the light emitting elements 11. For example, when the disposition height is low, since each of the light emitting elements 11 has a relatively small light emitting area, the number of light emitting elements 11 which are disposed should be relatively large, and when the disposition height is high, since each of the light emitting elements 11 has a relatively large light emitting area, the number of light emitting elements 11 which are disposed may be relatively small. However, in order to prevent damage to the escalator rail 200, the disposition height of each of the plurality of light emitting elements 11 may be roughly 3 cm to 10 cm from the escalator rail 200, and the disposition number may be 4 to 10. Further, FIG. 20 illustrates that the plurality of light emitting elements 11 are disposed in the light source part 10 in two stages, but is not limited thereto, and the light emitting elements 11 may also be disposed in one stage, three stages, or the like as necessary.

As points to be considered when the plurality of light emitting elements 11 are disposed in the light source part 10, the above-described disposition height and number as well as a disposition position are considered. Specifically, the plurality of light emitting elements 11 should be disposed at positions where emitted light of a predetermined wavelength does not reach the safety shield 31 which will be described later, this is because when one or more of the plurality of light emitting elements 11 is the UV LED, the safety shield 31 may be damaged.

In a description of FIG. 19 as an example, when any one or more of the plurality of light emitting elements 11 is the UV LED, the light emitting element 11 may be disposed in the two stages which is as far as possible from the safety shield 31 to prevent damage to the safety shield 31.

Meanwhile, since any one or more of the plurality of light emitting elements 11 may be the UV LED, the remaining light emitting elements 11 may be implemented with different colored LEDs, and thus, an aesthetic effect which allows soft light to leak out when driving the light source apparatus 100 according to the embodiment of the present invention may be realized.

The sensing part 20 may be disposed adjacent to the light source part 10.

Here, since adjacent disposition refers to disposition in front of the light source part 10, referring to FIGS. 19 and 20, it may be seen that the sensing part 20 is disposed in front of the light source part 10. Here, although a case in which the sensing part 20 is disposed in back of the light source part 10 may also be considered, since the sensing part 20 serves to sense an object which enters and exits through the opening 21 and thus should be disposed at both ends of the light source apparatus 100 according to the embodiment of the present invention, the case in which the sensing part 20 is disposed in back of the light source part 10 may not be considered.

Meanwhile, the sensing part 20 may include the opening 21 which opens some regions of the sensing part 20 to the outside and a sensing element 22 disposed at the opening 21 to generate sensing signals which senses the entry and exit of an object.

Here, as described above, since the opening 21 may be a path through which the object may enter and exit, although a case in which the opening 21 is not separately provided may be considered, when the light source apparatus 100 according to the embodiment of the present invention is installed on the rail 200 of the escalator without including the opening 21, the circulation of the rail 200 of the escalator may be interfered with. Actually, when a passenger boards the escalator and places his/her hand on the rail 200, the passenger may feel that the rail 200 of the escalator does not smoothly circulate and roughly circulates like passing some unevenness, and the rail 200 of the escalator rises by a predetermined height even if it is for a moment. In this case, when the light source apparatus 100 is installed without including the opening 21, the predetermined rising height may be covered, and since the rail 200 of the escalator directly comes into contact with the light source apparatus 100, the circulation of the rail 200 of the escalator may be interfered with, and the light source apparatus 100 may also be damaged. Accordingly, the opening 21 may be viewed as one of the essential components.

The opening 21 opens some region of the sensing part 20 to the outside and thus may be implemented in a form spaced apart from the rail 200 of the escalator by a predetermined height. Here, the predetermined height may be 2 cm to 5 cm in consideration of the rising height of the rail 200 of the escalator. In this case, the height of the opening 21 may be a height at which a passenger's hand may be suctioned, and a solution to this will be described later in a description of the safety shield 31.

Meanwhile, even when a passenger's hand is suctioned into the opening 21, although the safety shield 31 which will be described later may descend to prevent a personal injury, a secondary auxiliary unit which prevents the personal injury may be implemented in the opening 21. For example, as shown in FIG. 21, when a blocking shield 24 such as an awning, a vertical, a blind, or the like, made of a rubber material or the like is installed in the opening 21, since the passenger feels his/her hand touching the awning and thus may take his/her hand out before being suctioned into the light source apparatus 100, and the light source apparatus 100 may also conceal the inside, an effect of killing two birds with one stone may be obtained.

The sensing element 22 is disposed at the opening 21 to generate the sensing signals which sense the entry and exit of an object.

Here, the object refers to all types of objects regardless of type, and is a broad concept including even the passenger's hand using the escalator.

In this case, the sensing element 22 may be implemented as an infrared sensor which senses the entry and exit of an object by transmitting an infrared ray, and in addition, all known sensors may be used, but the sensing element 22 should be a sensor at least capable of sensing the entry and exit of an object.

Referring to FIG. 20, since it may be seen that the sensing element 22 is installed on a printed circuit board 23, the sensing signals generated by the sensing element 22 may be transmitted to a motor 32 which will be described later by the printed circuit board 23.

Meanwhile, since the sensing element 22 may more quickly sense the entry and exit of an object when disposed at a position as close as possible to the opening 21 rather than a distant position, the sensing element 22 may be disposed at a position as close as possible to the opening 21. However, this will differ according to the size and disposition position of the printed circuit board 23.

The blocking part 30 may be disposed between the light source part 10 and the sensing part 20.

Referring to FIG. 19, since it may be seen that the blocking part 30 is disposed between the light source part 10 on the right and the sensing part 20 on the left, the blocking part 30 may include the safety shield 31 which blocks the light source part 10 and the sensing part 20.

Here, the safety shield 31 is a component capable of preventing the entry and exit of the object to/from the opening 21, and more specifically, a case in which the a passenger's hand of the escalator is suctioned into the light source apparatus 100, and thus may be installed at a distance of 4 cm to 6 cm from the opening 21, and in this case, the passenger's hand suctioned through the opening 21 may be prevented from entering a relatively deep region of the light source apparatus 100.

Meanwhile, the safety shield 31 is driven in response to the sensing signals generated by the sensing element 22, and more specifically, may repeat vertical movement due to the motor 32.

Since FIG. 22 illustrates a normal state of the light source apparatus 100 according to another embodiment of the present invention, and FIG. 23 is a view illustrating a state of the light source apparatus 100 according to another embodiment of the present invention when a passenger's hand is suctioned through the opening 21, and when the passenger's hand is sensed by the sensing element 22 and thus the sensing signals are generated, the motor 32 connected thereto by the printed circuit board 23 is driven, and accordingly, an arm 33 of the motor 32 moves the safety shield 31 in a vertical direction.

More specifically, when the sensing signals generated by the sensing element 22 are received, the arm 33 of the motor 32 rotates up to 90° in a clockwise or counterclockwise direction to maximally move the safety shield 31 in a downward direction, and when the sensing signals generated by the sensing element 22 are not received, a state in which the safety shield 31 is maximally elevated is maintained. Here, the maximum 90° is an exemplary value, and may be changed according to a position at which the blocking part 30, more specifically, the safety shield 31 is disposed. Further, when the safety shield 31 maximally descends, the safety shield 31 may come into contact with or not come into contact with the rail 200 of the escalator. Here, when the safety shield 31 comes into contact with the rail 200 of the escalator, since a gap between the safety shield 31 and the rail 200 of the escalator is not formed, a problem of a passenger's hand being caught therebetween, which will be described later, does not occur, but a problem of driving of the escalator may occur due to contact.

Further, when the safety shield 31 does not come into contact with the rail 200 of the escalator, since the gap between the safety shield 31 and the rail 200 of the escalator is formed, the problem of a passenger's hand being caught therebetween may occur, but the problem may be solved by forming the gap very finely, and the problem of driving of the escalator may not occur due to non-contact. Accordingly, even when the safety shield 31 maximally descends, the safety shield 31 may not come into contact with the rail 200 of the escalator, but is not limited thereto.

The safety shield 31 which maximally descends by receiving the sensing signals generated by the sensing element 22, ascends as much as a degree of descending by receiving the sensing signals generated by the sensing element 22 when the sensing element 22 no longer senses the passenger's hand. That is, vertical movement is repeated according to the sensing signals.

Meanwhile, FIG. 23 illustrates a state in which the passenger's hand is suctioned through the opening 21, but the hand does not come into contact with the safety shield 31 and the safety shield 31 is in a maximally descended state. However, when the hand is quickly suctioned, as shown in FIG. 24, a case in which the passenger's hand is caught between the safety shield 31 and the rail 200 of the escalator may occur. In this case, the safety shield 31 continuously applies a force to the h passenger's hand to descend to the maximum position of descent, and accordingly, since the passenger's hand may be crushed, the safety shield 31 may be implemented as a flexible material such as rubber or the like to prevent the passenger's hand from being crushed.

So far, the light source apparatus 100 according to another embodiment of the present invention has been described. According to the present invention, even when a passenger places his/her hand on the rail 200 of the escalator, since the light source apparatus 100 senses the hand and thus the safety shield 31 descends before the hand is suctioned into the inside, a personal injury may be prevented, and when the light source apparatus 100 senses the passenger's hand, since the light emitting elements 11 are turned off, adverse effects on the human body in the case of the light emitting elements being UV LEDs may be fundamentally blocked.

Further, in the light source apparatus 100 according to another embodiment of the present invention, since maximally moving the safety shield 31 in the downward direction or stopping the driving of the escalator according to generation of the sensing signals from the sensing element 22 may be selected as modes, convenience of an escalator manager may be improved, and of course, the two functions may be simultaneously selected.

Meanwhile, as described above, when a passenger's hand is caught between the safety shield 31 and the rail 200 of the escalator, since the hand is suctioned into a relatively deep region of the light source apparatus 100 and thus an injury increases in the case in which the rail 200 of the escalator is continuously driven, in this case, the sensing signals generated by the sensing element 22 are transmitted to a controller (not shown) of the escalator to start or stop the driving of the escalator according to the sensing signals, and thus the injury may be prevented from increasing. That is, when the sensing element 22 senses the passenger's hand, the driving of the escalator is stopped, and since the driving of the escalator should be stopped as quickly as possible to prevent the injury from increasing after the passenger's hand is sensed, transmission of the sensing signals should be performed through a communication means having a high signal transmission speed.

Further, the light source apparatus 100 according to another embodiment of the present invention may further include a notification part 40 which outputs notification signals in response to the sensing signals generated by the sensing element 22, and the type of the notification signal can be anything such as visual, auditory, or the like. FIG. 25 illustrates a case in which voice-type notification signals are output through a speaker-type notification part 40, and FIG. 26 illustrates a case in which a fact that the personal injury occurs is output through a display-type notification part 40, and accordingly, other escalator passengers may recognize the occurrence of the personal injury and thus may request rescue from 119 or other rescue agencies.

Although the embodiments of the present invention are described with reference to the accompanying drawings, it should be understood by those skilled in the art that the present invention may be embodied in other various specific forms without changing its technical spirit or essential characteristics. Accordingly, the above-described embodiments of the present invention should be understood to be exemplary and not limiting.

The invention claimed is:

1. A light source apparatus comprising:
a housing;
a coupling unit configured to fix the housing to a target structure;
a light source module configured to emit light onto the target structure; and
a power source module configured to supply electrical power to the light source module,
wherein the light source module includes a first circuit board, a second circuit board disposed at one side of the first circuit board, a third circuit board disposed at the other side of the first circuit board,
wherein at least one first ultraviolet light emitting element is disposed on one surface of the first circuit board, at least one second ultraviolet light emitting element is disposed on one surface of the second circuit board, and at least one third ultraviolet light emitting element is disposed on one surface of the third circuit board,
wherein the light source module further includes a first heat dissipation plate and a second heat dissipation plate disposed to be spaced apart from each other and forming a cavity between the first heat dissipation plate and the second heat dissipation plate, and
wherein the at least one first ultraviolet light emitting element is disposed in the cavity.

2. The light source apparatus of claim 1, further comprising a first connector configured to connect the first circuit board and the second circuit board and a second connector configured to connect the first circuit board and the third circuit board.

3. The light source apparatus of claim 1, wherein the second ultraviolet light emitting element and the third ultraviolet light emitting element emit ultraviolet light onto side surfaces of the target structure.

4. The light source apparatus of claim 1, wherein:
the one surface of the second circuit board and the one surface of the third circuit board are disposed to face each other,
the first heat dissipation plate includes a first inclined surface;
the second heat dissipation plate includes a second inclined surface facing the first inclined surface; and
an interval between the first inclined surface and the second inclined surface increases as a distance from the first circuit board increases.

5. The light source apparatus of claim 4, wherein:
the first heat dissipation plate includes a plurality of first heat dissipation fins connected to the first inclined surface;
the second heat dissipation plate includes a plurality of second heat dissipation fins connected to the second inclined surface; and
the plurality of first heat dissipation fins and the plurality of second heat dissipation fins are disposed in parallel with the first circuit board.

6. The light source apparatus of claim 4, wherein:
the first heat dissipation plate includes a plurality of first heat dissipation fins protruding toward the target structure;
the second heat dissipation plate includes a plurality of second heat dissipation fins protruding toward the target structure;
each of the plurality of first heat dissipation fins has the same inclination angle as the first inclined surface;
each of the plurality of second heat dissipation fins has the same inclination angle as the second inclined surface; and
a minimum interval between the target structure and the first heat dissipation plate is smaller than a minimum interval between the target structure and the first ultraviolet light emitting element.

7. The light source apparatus of claim 3, further comprising a support frame coupled to the first to third circuit boards,
wherein the support frame includes a support plate to which the first to third circuit boards are fixed, a fixing plate configured to fix the support plate to the housing, and a connection part configured to connect the support plate and the fixing plate,
wherein the fixing plate includes a first hole coupled to a screw, and
wherein the first hole extends in a first direction.

8. The light source apparatus of claim 7, wherein:
the support plate includes a first hole disposed in a region where the first circuit board is fixed; and
the light source module includes a third heat dissipation plate thermally connected to the first circuit board through the first hole.

9. The light source apparatus of claim 1, wherein the light source module includes a support frame configured to fix the first to third circuit boards to the housing, and a position adjusting part configured to adjust a position where the support frame is fixed to the housing.

10. The light source apparatus of claim 1, further comprising a sensing part disposed adjacent to the light source module, and a blocking part disposed between the light source module and the sensing part,
wherein the sensing part includes an opening configured to open some region of the sensing part to the outside, and a sensing element disposed at the opening to generate a sensing signal which senses the entry and exit of an object,
wherein the blocking part includes a safety shield configured to block the sensing part and the light source module, and
wherein the safety shield is driven in response to the sensing signal generated from the sensing element.

11. The light source apparatus of claim 1, wherein:
the first circuit board includes heat conductive pad portions disposed at both sides thereof in a first direction which is an extending direction of the first circuit board, a circuit pattern electrically connected to the at least one ultraviolet light emitting element, and an insulation layer disposed on the circuit pattern;
the heat conductive pad portions are coplanarly disposed with the circuit pattern; and
the first heat dissipation plate and the second heat dissipation plate come into contact with the heat conductive pad portions.

12. The light source apparatus of claim 1, wherein:
the target structure includes a hand rail; and
the housing includes an inlet and an outlet through which a rotating rail of the target structure passes.

13. The light source apparatus of claim 12, wherein the power source module includes a roller rotated by the hand rail, and a power supply rotated by the roller to generate power.

14. The light source apparatus of claim 13, wherein:
the roller and the power supply are disposed in a direction from the inlet toward the outlet; and
the roller is disposed farther from the inlet than the power supply.

15. The light source apparatus of claim 13, further comprising an elastic member configured to connect the power source module to the housing,
wherein the elastic member restores the roller to an original position when the roller is spaced apart from the rotating rail.

16. The light source apparatus of claim 1, further comprising a case disposed on the housing.

17. The light source apparatus of claim 1, wherein an angle formed by a first direction which is an extending direction of the first circuit board and a second direction which is an extending direction of the second circuit board is smaller than 180°.

18. The light source apparatus of claim 1, wherein the light source module emits ultraviolet light onto an upper surface and side surfaces of the target structure to perform sterilization.

19. A light source apparatus comprising:
a housing;
a coupling unit configured to fix the housing to a target structure;
a light source module configured to emit light onto the target structure; and
a power source module configured to supply electrical power to the light source module,
wherein the light source module includes a first circuit board, a second circuit board disposed at one side of the first circuit board, a third circuit board disposed at the other side of the first circuit board,
wherein at least one first ultraviolet light emitting element is disposed on one surface of the first circuit board, at least one second ultraviolet light emitting element is disposed on one surface of the second circuit board, and at least one third ultraviolet light emitting element is disposed on one surface of the third circuit board,
wherein the housing includes an inlet and an outlet through which a rotating rail of the target structure passes, a first brush disposed at the inlet of the housing, and a second brush disposed at the outlet of the housing,
wherein the first brush includes an elongated hole for adjustably coupling the first brush a predetermined distance from the rotating rail, and
wherein the second brush includes an elongated hole for adjustably coupling the second brush a predetermined distance from the rotating rail.

20. The light source apparatus of claim 19, wherein each of the first brush and the second brush is formed of an elastic material.

* * * * *